(12) United States Patent
Sniffin

(10) Patent No.: US 8,162,895 B2
(45) Date of Patent: Apr. 24, 2012

(54) ENDOLUMINAL ACCESS DEVICE

(75) Inventor: Kevin Sniffin, Danbury, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 363 days.

(21) Appl. No.: 12/358,684

(22) Filed: Jan. 23, 2009

(65) Prior Publication Data

US 2009/0192466 A1    Jul. 30, 2009

Related U.S. Application Data

(60) Provisional application No. 61/023,644, filed on Jan. 25, 2008.

(51) Int. Cl.
*A61M 5/178* (2006.01)

(52) U.S. Cl. .......... 604/167.01; 604/167.06; 604/170.02

(58) Field of Classification Search ............ 604/167.01, 604/167.11, 284, 164.01–164.13, 167.06, 604/170.01–170.02, 171; 600/154, 164, 600/121, 130, 136, 138–139, 143
See application file for complete search history.

(56) References Cited

U.S. PATENT DOCUMENTS

| | | | |
|---|---|---|---|
| 1,459,313 A | 6/1923 | Reisler et al. | |
| 4,706,656 A | 11/1987 | Kuboto | |
| 4,869,238 A | 9/1989 | Opie et al. | |
| 5,059,183 A | 10/1991 | Semrad | |
| 5,386,814 A | 2/1995 | Jones | |
| 5,941,852 A * | 8/1999 | Dunlap et al. | 604/164.11 |
| 6,352,503 B1 | 3/2002 | Matsui et al. | |
| 6,520,975 B2 * | 2/2003 | Branco | 606/159 |
| 2004/0230096 A1 | 11/2004 | Stefanchik et al. | |
| 2006/0020241 A1 * | 1/2006 | Piskun et al. | 604/93.01 |
| 2006/0235457 A1 * | 10/2006 | Belson | 606/191 |
| 2008/0188869 A1 * | 8/2008 | Weitzner et al. | 606/130 |

OTHER PUBLICATIONS

International Search Report for PCT/US09/31848 date of completion is Mar. 5, 2009 (9 pages).

\* cited by examiner

*Primary Examiner* — Nicholas Lucchesi
*Assistant Examiner* — Melissa A Snyder

(57) ABSTRACT

A surgical access apparatus for providing access inside a body includes a housing having a first port, a tubular member extending distally from the housing and defining a longitudinal axis therealong, wherein the tubular member includes a lumen extending therethrough. a shaft insert disposed in the lumen of the tubular member, wherein the shaft insert forms first, second, and third passageways extending along the lumen of the tubular member, wherein each of the first, second, and third passageways is adapted to receive a surgical instrument; and a first seal assembly covering the first port of the housing and defining a first passage disposed in communication with the first passageway defined by the shaft insert in the tubular member, wherein the first seal assembly is adapted to form a seal around the surgical instrument inserted through the first passage of the first seal assembly.

20 Claims, 17 Drawing Sheets

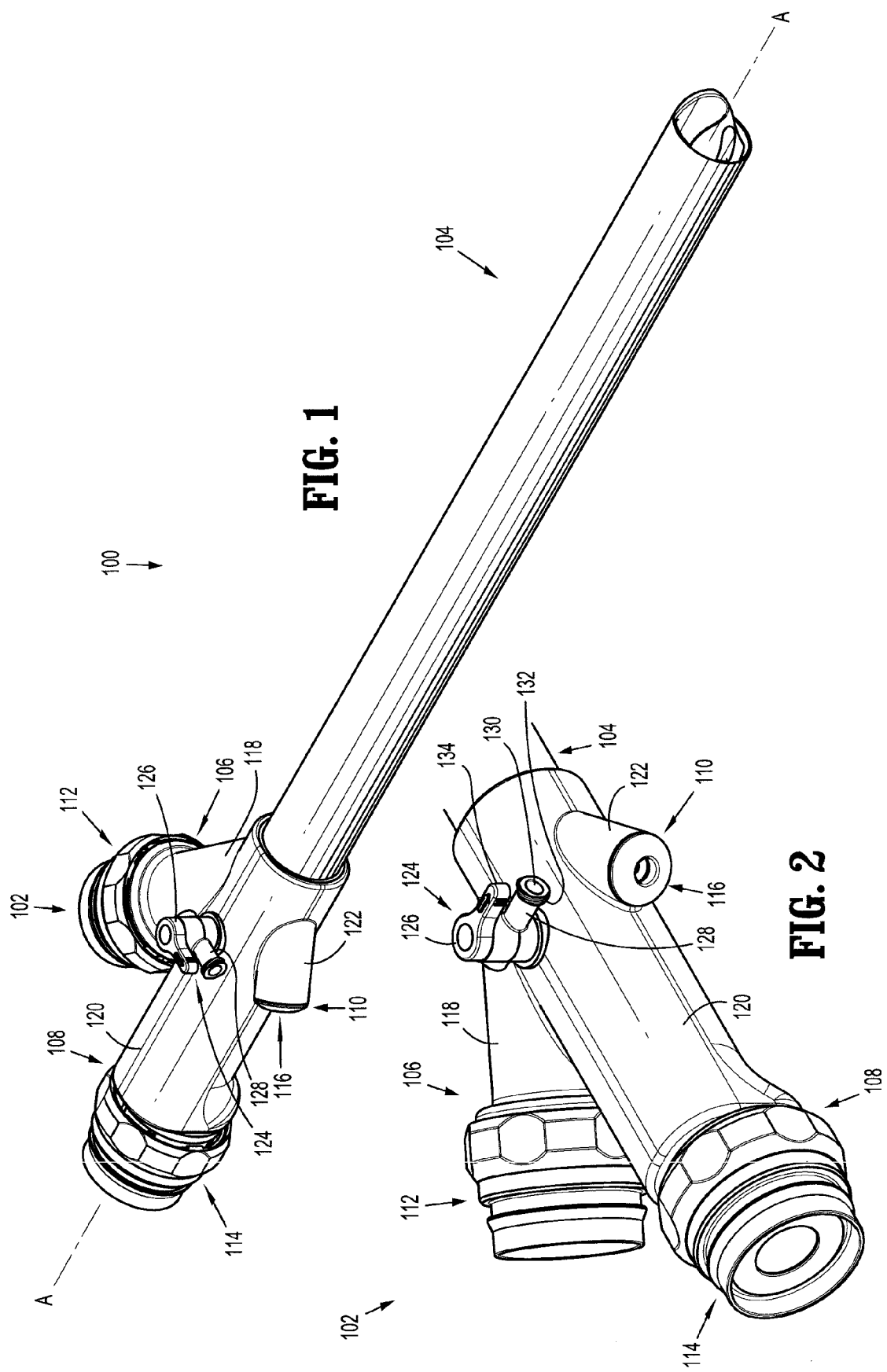

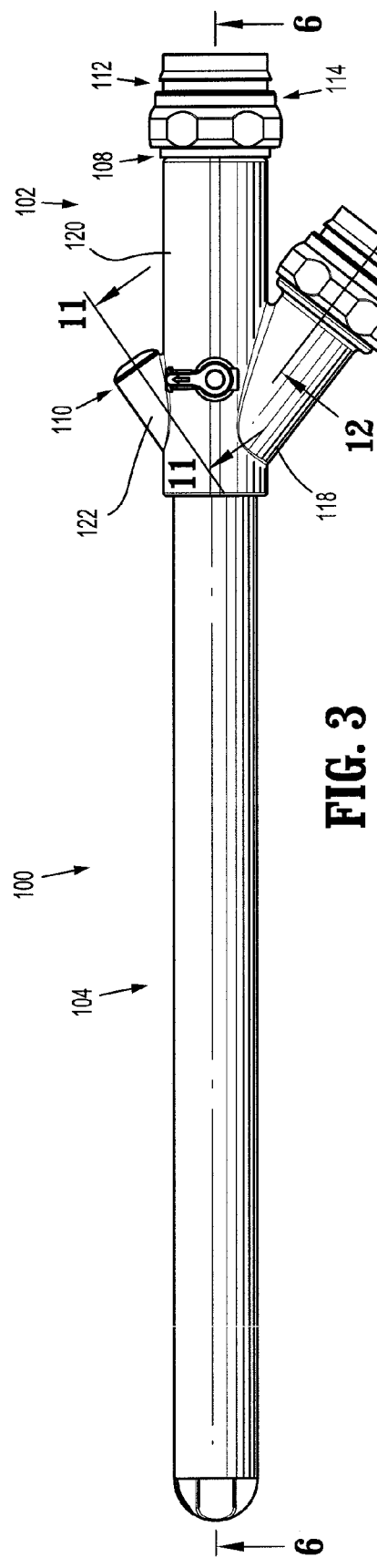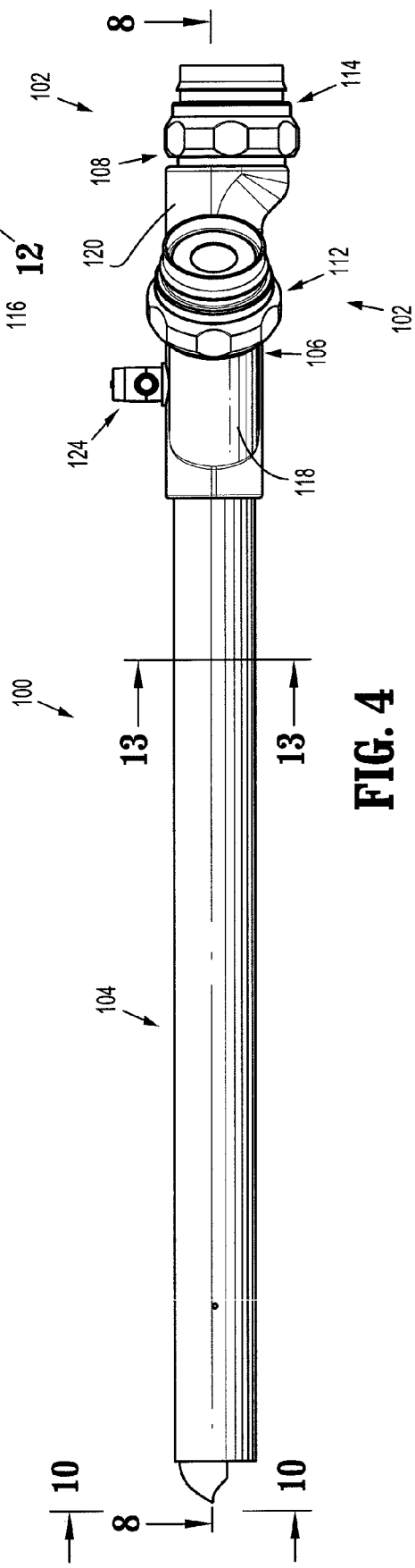

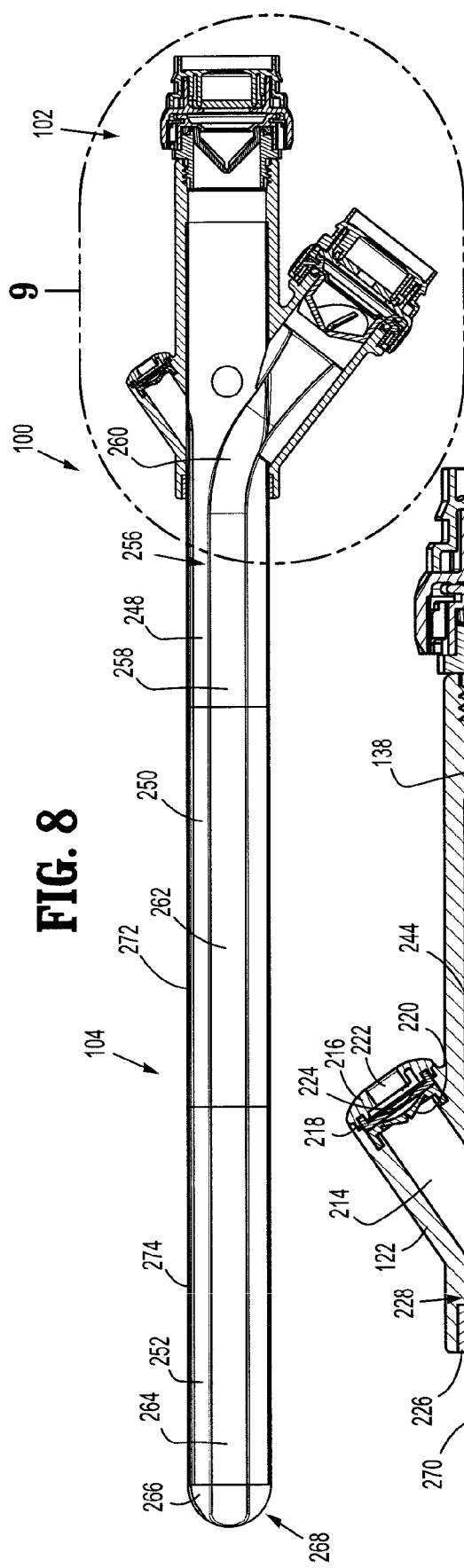
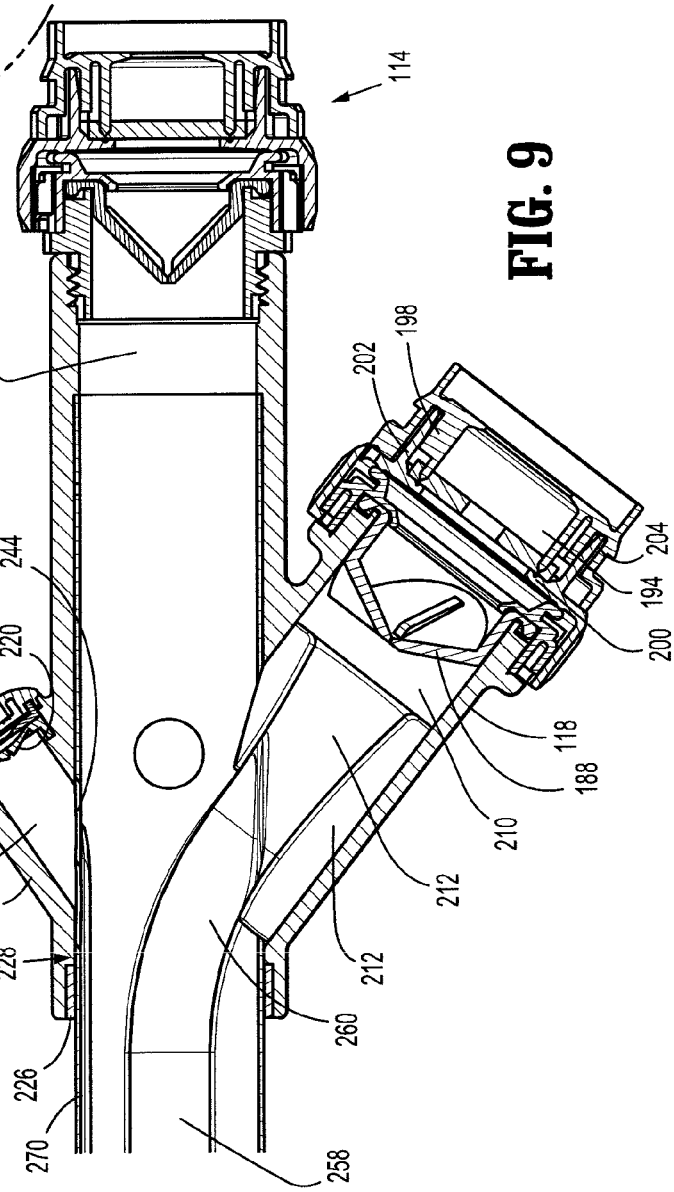
FIG. 8
FIG. 9

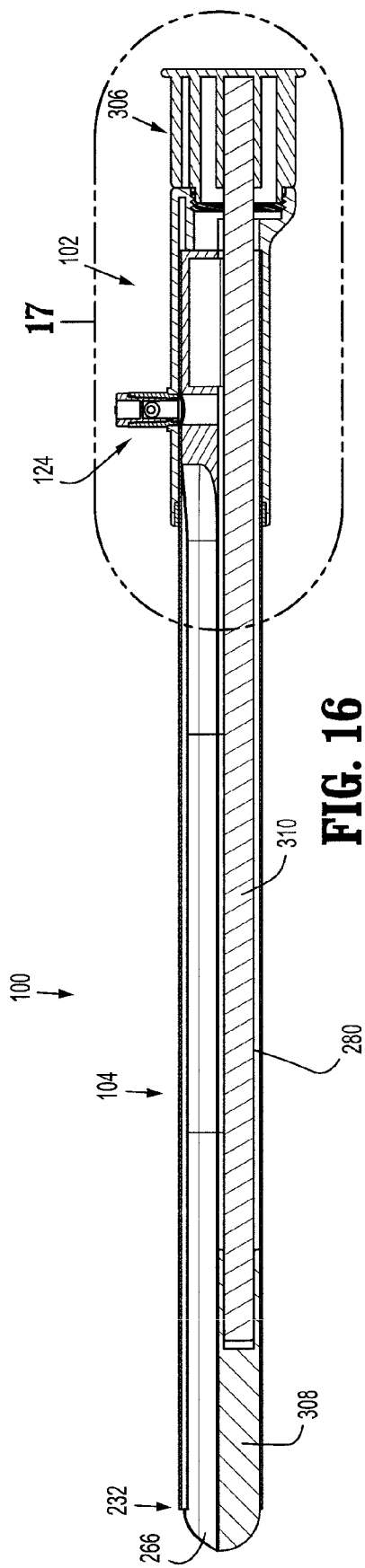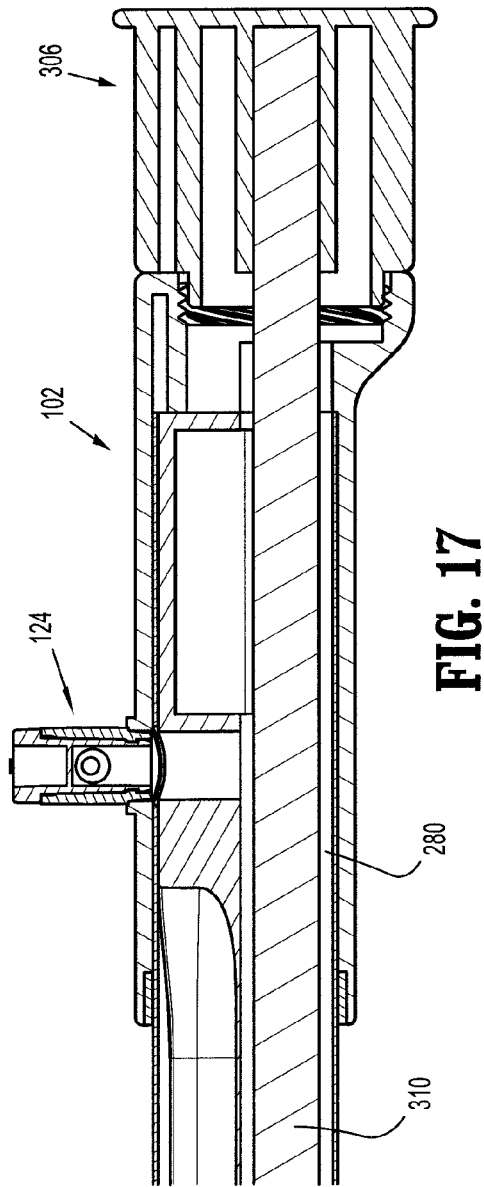

ENDOLUMINAL ACCESS DEVICE

CROSS-REFERENCE TO RELATED APPLICATION

This applications claims priority to and the benefit of U.S. Provisional Patent Application 61/023,644, filed on Jan. 25, 2008, which is incorporated by reference in its entirety.

BACKGROUND

1. Technical Field

The present disclosure relates to surgical instruments and methods. More particularly, the present disclosure relates to an endoluminal access device.

2. Background of Related Art

Endoluminal surgery encompasses all surgical procedures that involve intentional instrument penetration into a lumen of a human body, such as vascular lumens, gastrointestinal lumens, or air exchange lumens. For example, endoluminal surgery may be performed by introducing a surgical instrument through the esophagus, rectum, vagina, urethra or bladder. These procedures generally entail diagnosis or treatment of diseases or debilitating conditions. Surgeons usually utilize a rigid or flexible tube, such as an endoscope, during endoluminal surgery. The tube is normally introduced into the human body through a body orifice, such as the mouth or rectum, or through an incision. Endoscopes allow surgeons to view the target surgical site and may provide one or more working channels, or pathways, to the treatment site. During endoluminal surgical procedures, the surgeon steers or places the endoscope through the body until it reaches the intended site. Thereafter, the surgeon may perform the appropriate medical procedure.

SUMMARY

A surgical access apparatus for providing access inside a body includes a housing having a first port, a tubular member extending distally from the housing and defining a longitudinal axis therealong, wherein the tubular member includes a lumen extending therethrough. a shaft insert disposed in the lumen of the tubular member, wherein the shaft insert forms first, second, and third passageways extending along the lumen of the tubular member, wherein each of the first, second, and third passageways is adapted to receive a surgical instrument; and a first seal assembly covering the first port of the housing and defining a first passage disposed in communication with the first passageway defined by the shaft insert in the tubular member, wherein the first seal assembly is adapted to form a seal around the surgical instrument inserted through the first passage of the first seal assembly.

In one embodiment, the tubular member is made of a one of rigid material and a flexible material.

In one embodiment, the housing includes a first tubular portion defining an axis that is at an oblique angle relative to the longitudinal axis of the tubular member.

In one embodiment, the first tubular portion of the housing includes a bore disposed in fluid communication with the first port.

In one embodiment, the housing includes a second port and a third port, each of the second and third ports being adapted to receive a surgical instrument.

In one embodiment, wherein the housing includes a second tubular portion having a bore, the bore being disposed in communication with the second port and the second passageway.

In one embodiment, the second tubular portion of the housing defines an axis that is oriented substantially parallel to the longitudinal axis of the tubular member.

In one embodiment, the access apparatus further includes a second seal assembly releasably connected to the second tubular portion of the housing, the second seal assembly having passage disposed in communication with the second passageway, wherein the seal assembly is adapted to form a seal around a surgical instrument inserted through the second passage.

In one embodiment the second passageway is configured to receive an obturator in the absence of the second seal assembly.

In one embodiment, the housing includes a third tubular portion having a bore, the bore being disposed in communication with the third port and the third passageway.

In one embodiment, the third tubular portion of the housing defines an axis that is at an oblique angle relative to the longitudinal axis of the tubular member.

In one embodiment, the third passageway is configured to receive an endoscope.

The present application further relates to another embodiment of a surgical access apparatus for providing access inside a body. This embodiment includes a housing having a first port, a tubular member extending distally from the housing and defining a longitudinal axis therealong, wherein the tubular member includes a lumen extending therethrough, a dividing wall positioned along the lumen of the tubular member, the dividing wall having a substantially S-shaped transverse cross-sectional profile, wherein the substantially dividing wall divides the lumen into first and second passageways, wherein each of the first and second passageways is adapted to receive a surgical instrument, and a first seal assembly covering the first port of the housing and defining a first passage disposed in communication with the first passageway defined by the shaft insert in the tubular member, wherein the first seal assembly is adapted to form a seal around the surgical instrument inserted through the first passage of the first seal assembly.

In one embodiment, the tubular member is made of a one of rigid material and a flexible material.

In one embodiment, the housing includes a first tubular portion defining an axis that is at an oblique angle relative to the longitudinal axis of the tubular member.

In one embodiment, the first tubular portion of the housing includes a bore disposed in fluid communication with the first port.

In one embodiment, the housing includes a second port and a third port, each of the second and third ports being adapted to receive a surgical instrument.

In one embodiment, the housing includes a second tubular portion having a bore, the bore being disposed in communication with the second port and the second passageway.

In one embodiment, the second tubular portion of the housing defines an axis that is oriented substantially parallel to the longitudinal axis of the tubular member.

In one embodiment, the dividing wall is made of at least one of a flexible and resilient material.

BRIEF DESCRIPTION OF THE DRAWINGS

Embodiments of the presently disclosed access device are described herein with reference to the accompanying drawings, wherein:

FIG. 1 is a perspective view of an access apparatus according to an embodiment of the present disclosure;

FIG. 2 is a perspective view of a proximal portion of the access apparatus shown in FIG. 1;

FIG. 3 is a top view of the access apparatus shown in FIG. 1;

FIG. 4 is a side view of the access apparatus shown in FIG. 1;

FIG. 8 is a top cross-sectional view of the access apparatus shown in FIG. 1, taken along section line 8-8 of FIG. 4;

FIG. 9 is an enlarged view of the indicated area of detail of FIG. 8;

FIG. 16 is a side cross-sectional view of the access apparatus and obturator shown in FIG. 15, taken along section line 16-16 of FIG. 15;

FIG. 17 is an enlarged view of the indicated area of detail of FIG. 16;

DETAILED DESCRIPTION OF THE EMBODIMENTS

Figure 5:
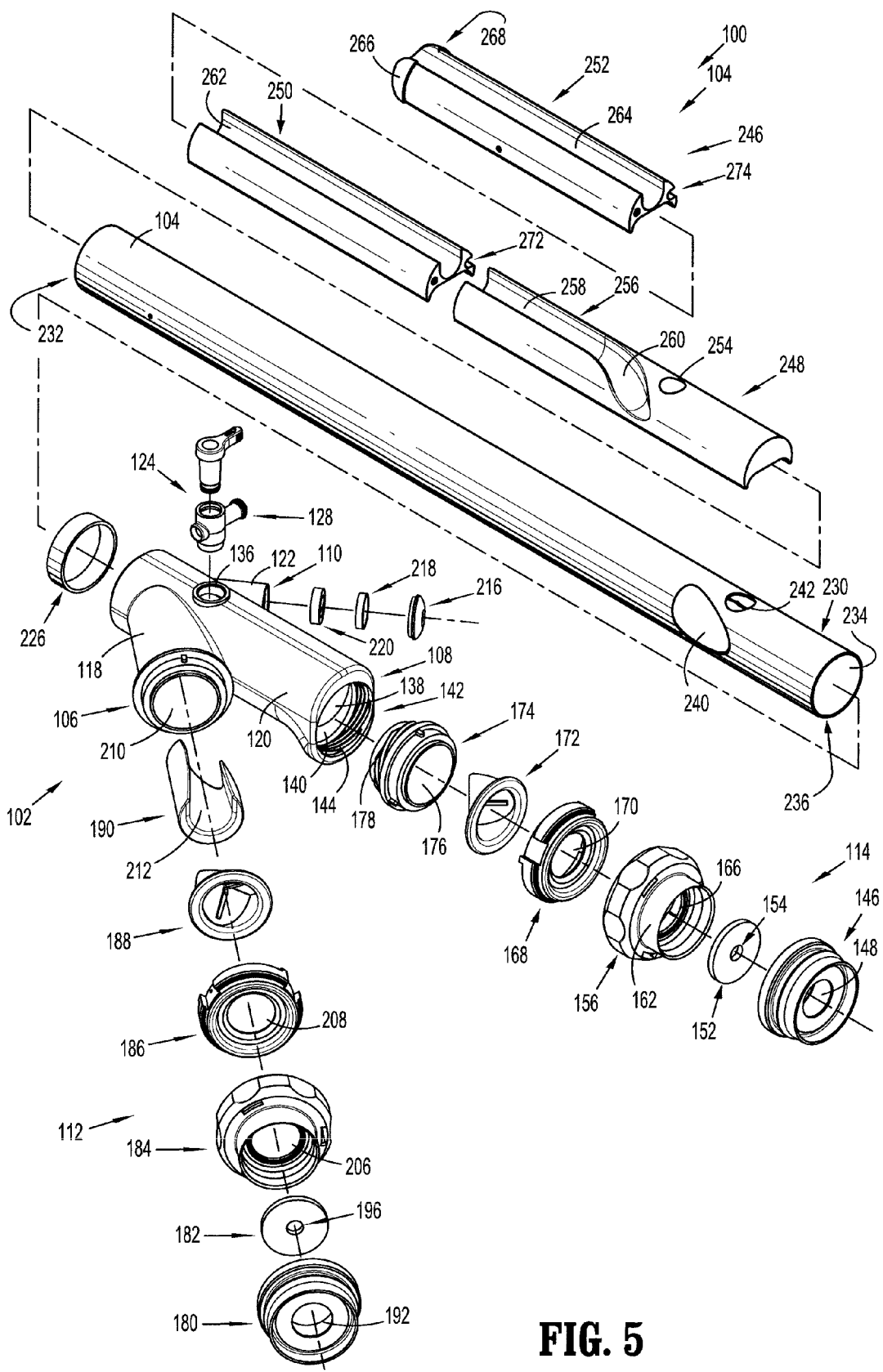
FIG. 5 is a perspective view, with parts separated, of the access apparatus shown in FIG. 1.

Embodiments of the presently disclosed access apparatus will now be described in detail with reference to the drawings wherein like reference numerals identify similar or identical elements. In the drawings and in the description which follows, the term "proximal," as is traditional, will refer to the end of the access apparatus that is closest to the operator, while the term "distal" will refer to the end of the access apparatus that is farthest from the operator. In the present disclosure, the words "a," "an," or "the" are to be taken to include both the singular and the plural. Similarly, any reference to plural items shall, where appropriate, include the singular.

The present disclosure relates to an endoluminal access apparatus for use in surgical procedures. The access apparatus provides access to a working space inside a human body. Physicians can utilize the presently disclosed access device in many kinds of surgical procedures including, but not limited to, endoluminal, transvaginal, endoscopic and laparoscopic procedures. In addition, the access apparatus of the present disclosure can be employed in combination with any suitable surgical instrument.

Referring initially to FIGS. 1-4, an access apparatus is generally designated with reference numeral 100. Access apparatus 100 includes a housing 102 and a shaft or tubular member 104. In one embodiment, tubular member 104 is made of a rigid material. Tubular member 104 extends distally from housing 102 and defines a longitudinal axis A-A therealong. Housing 102 includes a first tubular portion 118, a second tubular portion 120, and a third tubular portion 122. Second tubular portion 120 is oriented substantially parallel to longitudinal axis A-A, whereas first and third tubular portions 118, 122 each define an axis that is at an oblique angle relative to longitudinal axis A-A. First and third tubular portions 118, 122 converge into second tubular portion 120 of housing 102.

First tubular portion 118 of housing 102 defines a first port 106 adapted to receive a surgical instrument. Second tubular portion 120 defines a second port 108 configured to receive a surgical instrument. Third tubular portion 122 defines a third port 110 adapted to receive a surgical instrument. Each of the first port 106, second port 108, and third port 110 provides a passage into an inner portion of housing 102.

Housing 102 further includes first, second, and third seal assemblies 112, 114, 116, respectively. Each of the first, second and third seal assemblies 112, 114, 116 covers first port 106, second port 108, and third port 110, respectively. As will be discussed in detail below, first, second, and third seal assemblies 112, 114, 116 form a seal around a surgical instrument when said surgical instrument is inserted through first, second, and third ports 106, 108, 110, respectively. Also, second and third seal assemblies 114, 116 are configured to remain closed in the absence of a surgical instrument extending therethrough.

In addition to seal assemblies 112, 114, 116, housing 102 includes an insufflation assembly 124 configured to be connected to a source of insufflation gases or a vacuum system (not shown). Insufflation assembly 124 incorporates an insufflation port 128 and a stop-cock valve 126. Insufflation port 128 defines a lumen 130 disposed in fluid communication with an inner portion of housing 102 and includes an external thread 132 for facilitating connection to a source of insufflation gases or a vacuum system.

Stopcock valve 126 has an open position and a closed position. Thus, stopcock valve 126 is capable of controlling fluid flow through insufflation assembly 124. In the open position, stopcock valve 126 allows fluid flow through insufflation assembly 124. In the closed position, stopcock valve 126 prevents or hinders fluid flow through insufflation assembly 124. In one embodiment, stopcock valve 126 includes a lever 134 extending therefrom. Lever 134 facilitates rotation of stopcock valve 126 with respect to housing 202. In use, a user actuates stopcock valve 126 between the open and closed positions by rotating stopcock valve 126 relative to housing 102 through lever 134. While a stopcock valve is shown and described, it is envisioned that any suitable valve capable of permitting and restricting fluid flow, may be provided in insufflation assembly 124.

With reference to FIGS. 5-9, housing 102 defines an opening 136 configured to receive a portion of insufflation assembly 124. Opening 136 is disposed in fluid communication with insufflation port 128 and allows fluid flow between a source of insufflation gases or a vacuum system and an inner portion of housing 102 when insufflation port 128 is fluidly coupled to the source of insufflation gases or vacuum system. In the depicted embodiment, opening 136 is positioned on second tubular portion 120 of housing 102. It is contemplated that opening 136 can nevertheless be located on any part of housing 102.

As seen in FIGS. 5-9, first seal assembly 112 is fixed to first tubular portion 118 of housing 102. First seal assembly 112 includes a cover 180, an instrument seal 182, a knob 184, a seal cover 186, and a duckbill valve 188. Cover 180 defines an opening 192 extending therethrough. Opening 192 is dimensioned to receive a surgical instrument and leads to an inner cavity 194 (see FIG. 9) of cover 180. Inner cavity 194 is configured to receive instrument seal 182. Instrument seal 182 defines an aperture 196 extending therethrough. Aperture 196 is dimensioned to receive a surgical instrument. In operation, instrument seal 182 forms a fluid-tight seal around a surgical instrument when the surgical instrument is inserted through aperture 196.

First seal assembly 114 can be connected to port 106 by snapping knob 184s onto port 106. It is envisioned, however, that first seal assembly 112 may be connected to port 106 by any suitable means. When first seal assembly 112 is assembled, instrument seal 182 is located between cover 180 and knob 184. As seen in FIG. 9, cover 180 includes a ring 198 protruding distally therefrom. Ring 198 presses instrument seal 182 against a proximal wall 200 of knob 184. Knob 184 includes a ring 202 protruding proximally therefrom. Ring 202 is adapted to be received inside an annular space 204 formed in cover 180. During assembly, ring 202 is positioned inside annular space 204 to facilitate interconnection between cover 180 and knob 184.

Knob 184 further includes a longitudinal opening 206 configured to receive a surgical instrument and at least a portion of seal cover 186. Seal cover 186 includes a hole 208 adapted to receive a surgical instrument and, during operation, aids in securing duckbill valve 188 to first seal assembly 112 and first tubular member 118. Duckbill valve 188 is partially disposed in a bore 210 of first tubular portion 118. In operation, duckbill valve 188 forms a fluid-tight seal around a surgical instrument inserted therethough and closes in the absence of a surgical instrument extending therethrough.

As discussed above, duckbill valve 188 is positioned in bore 210 of first tubular portion 118. Bore 210 extends through first tubular portion 118 and is dimensioned to receive not only duckbill valve 188 but also a surgical instrument and a lead-in insert 190. During use, lead-in insert 190 guides the insertion of a surgical instrument through first tubular portion 118. Lead-in insert 190 is in the form of a C-shaped channel and defines a passage 212 therealong. Passage 212 is dimensioned to slidably receive a surgical instrument such as an endoscope. During use, passage 212 of lead-in insert 190 steers a surgical instrument inserted through first tubular portions 118 toward second tubular portion 120 of housing 202.

As seen in FIGS. 5-9, second tubular portion 120 of housing 102 has inner surfaces 140 forming a bore 138. Bore 138 extends through second tubular portion 120 and is dimensioned to receive a portion of tubular member 104 and a portion of first seal assembly 114. Second tubular portion 120 additionally includes an inner thread 144 formed about a proximal end 142 of inner surfaces 140. Inner thread 144 is adapted to threadedly engage a portion of second seal assembly 114.

Figure 7:
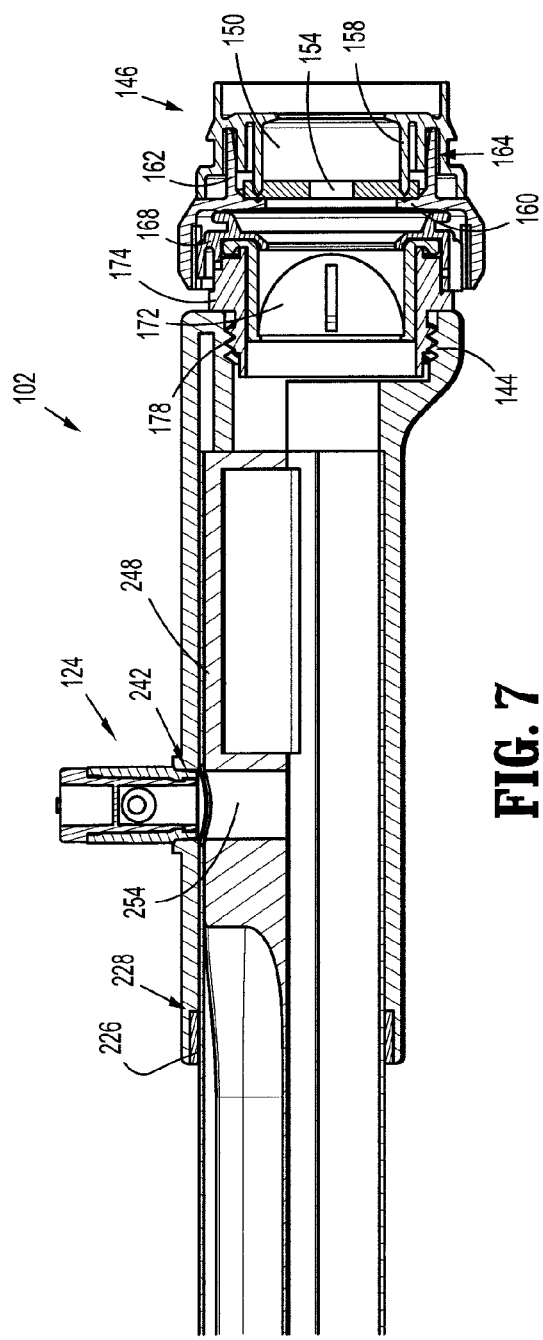
FIG. 7 is an enlarged view of the indicated area of detail of FIG. 6.

Second seal assembly 114 covers second port 108 and includes a cover 146 defining an opening 148. Opening 148 extends through cover 146 and is dimensioned to receive a surgical instrument. Moreover, opening 148 leads to an inner cavity 150, as seen in FIG. 7, defined in cover 146. Inner cavity 150 of cover 146 is configured to receive an instrument seal 152.

Instrument seal 152 defines an aperture 154 dimensioned to receive a surgical instrument. In use, instrument seal 152 forms a fluid-tight seal around a surgical instrument inserted through aperture 154. When second seal assembly 114 is assembled, instrument seal 152 is positioned between cover 146 and knob 156. Cover 146 includes a ring 158 protruding distally therefrom, as seen in FIG. 7. Ring 158 presses instrument seal 152 against a proximal wall 160 of knob 156, thereby securing instrument seal 152 between cover 146 and knob 156. Knob 156 includes a ring 162 protruding proximally therefrom. Ring 162 is adapted to be received within an annular space 164 formed in cover 146. During assembly, ring 162 is placed within annular space 164 to facilitate interconnection between cover 146 and knob 156.

Knob 156 further includes a longitudinal opening 166 configured to receive a surgical instrument and at least a portion of a seal cover 168. Seal cover 168 includes a hole 170 adapted to receive a surgical instrument and, during use, helps secure a duckbill valve 172 within second seal assembly 114. Duckbill valve 172 is disposed between seal cover 168 and a threaded adapter 174. Duckbill valve 172 is adapted to form a fluid-tight seal around a surgical instrument inserted therethrough and close in the absence of a surgical instrument extending therethrough. A portion of duckbill 175 is located inside threaded adapter 174.

With continued reference to FIGS. 5-9, threaded adapter 174 releasably secures second seal assembly 114 to second tubular portion 120 of housing 102. Threaded adapter 174 includes an external thread 178 formed thereabout and a longitudinal bore 176 adapted to receive a surgical instrument and at least a portion of duckbill seal 175. External thread 178 is configured to threadedly engage inner thread 144 of second tubular portion 120. In operation, the user can release or attach second seal assembly 113 to second tubular portion 120 by inserting at least a portion of threaded adapter 174 in bore 138 of second tubular portion 120 and then rotating second seal assembly 114, via knob 156, with respect to second tubular portion 120. While second seal assembly 114 rotates relative to second tubular portion 120, external thread 178 engages or disengages inner thread 144. When external thread 178 engages inner thread 144, second seal assembly 114 is connected to second tubular portion 120. Conversely, second seal assembly 114 detaches from second tubular portion 120 when external thread 178 disengages from inner thread 144 of second tubular portion 120 of housing 202.

As seen in FIG. 9, third tubular portion 122 of housing 202 defines a bore 214 dimensioned to receive a surgical instrument. Bore 214 is disposed in fluid communication with third port 110. Third seal assembly 116 covers third port 110 and includes a cap 216, an instrument seal 218, and a duckbill valve 220. Cap 216 has a hole 222 extending therethrough. Hole 222 is dimensioned to receive a surgical instrument and leads to bore 214 of third tubular portion 122. Instrument seal 218 is secured between cap 216 and duckbill valve 220 and defines an opening 224. Opening 224 is configured to receive a surgical instrument. In use, instrument seal 218 forms a fluid-tight seal around a surgical instrument inserted through opening 224. Duckbill valve 220 is adapted to form a fluid-tight seal around a surgical instrument inserted therethrough and close in the absence of a surgical instrument extending therethrough.

As seen in FIG. 9, access apparatus 100 further includes a compression ring 226 adapted to be disposed in a distal end 228 of bore 138 of second tubular portion 120. When access apparatus 100 is assembled, compression ring 226 is positioned between housing 102 and tubular member 104. Compression ring 226 compresses tubular member 104 inwardly, thus securing tubular member 104 to housing 104.

As seen in FIGS. 5-9, tubular member 104 has a proximal portion 230 and a distal portion 232 Moreover, tubular member 104 includes a proximal opening 236, a distal opening 238 and a lumen 234 extending therethrough. Lumen 234 fluidly couples proximal and distal openings 236, 238. Proximal portion 230 of tubular member 104 is disposed within bore 138 of second tubular portion 120 of housing 202. Proximal portion 230 of tubular member 104 includes an aperture 240 for establishing fluid communication between bore 210 of first tubular portion 118 and lumen 234 of tubular member 104, an opening 242 for establishing fluid communication between insufflation assembly 124 and lumen 234, and a hole 244 (see FIG. 9) for establishing fluid communication between bore 214 of third tubular portion 122 and lumen 234. When proximal portion 230 of tubular member 104 is positioned within housing 102, aperture 240 is aligned with bore 210 of first tubular portion 118, opening 242 is aligned with hole 136 of second tubular portion 120, and hole 244 is aligned with bore 214 of third tubular portion 122.

As seen in FIGS. 5-9, access apparatus 100 further includes a shaft insert 246 adapted to be disposed in lumen 234 of tubular member 104. Shaft insert 246 includes a proximal insertion member 248, a middle insertion member 250, and a distal insertion member 252. Proximal, middle, and distal insertion members 248, 250, 252 are interconnected. Each of the proximal, middle, and distal insertion members 248, 250, 252 is adapted to be inserted inside lumen 234 of tubular member 104.

Figure 12:
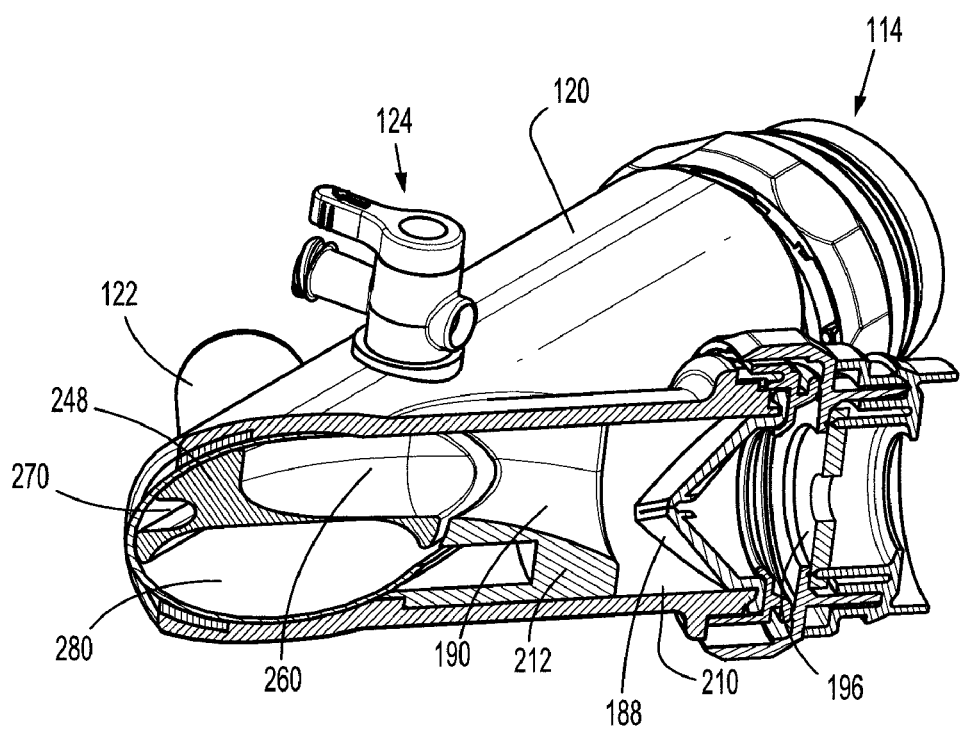
FIG. 12 is a perspective cross-sectional view of the access apparatus shown in FIG. 1, taken along section line 12-12 of FIG. 3.
Figure 13:
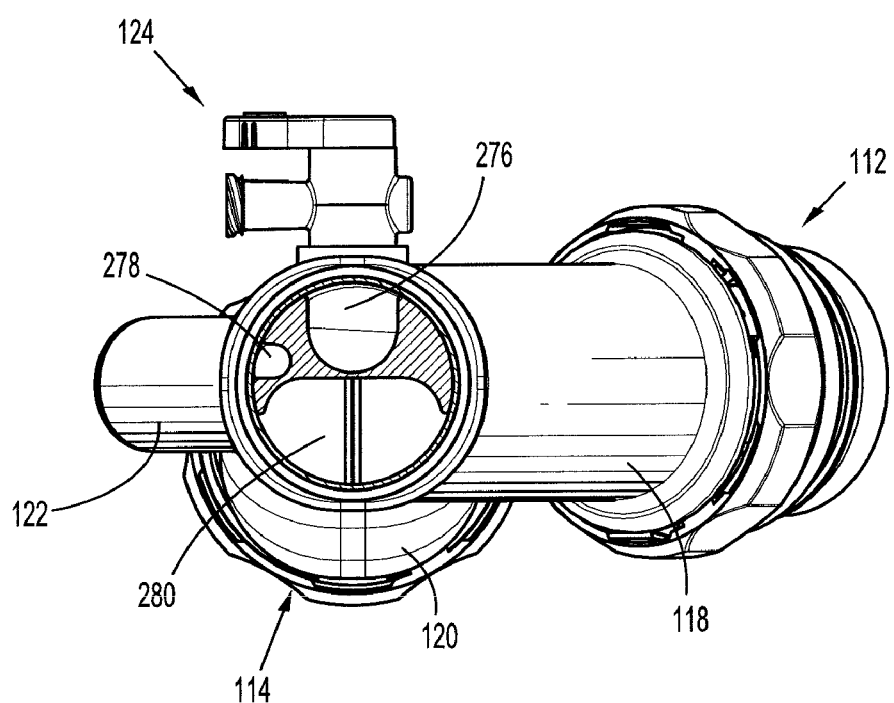
FIG. 13 is a front cross-sectional view of the access apparatus shown in FIG. 1, taken along section line 13-13 of FIG. 4.
Figure 14:
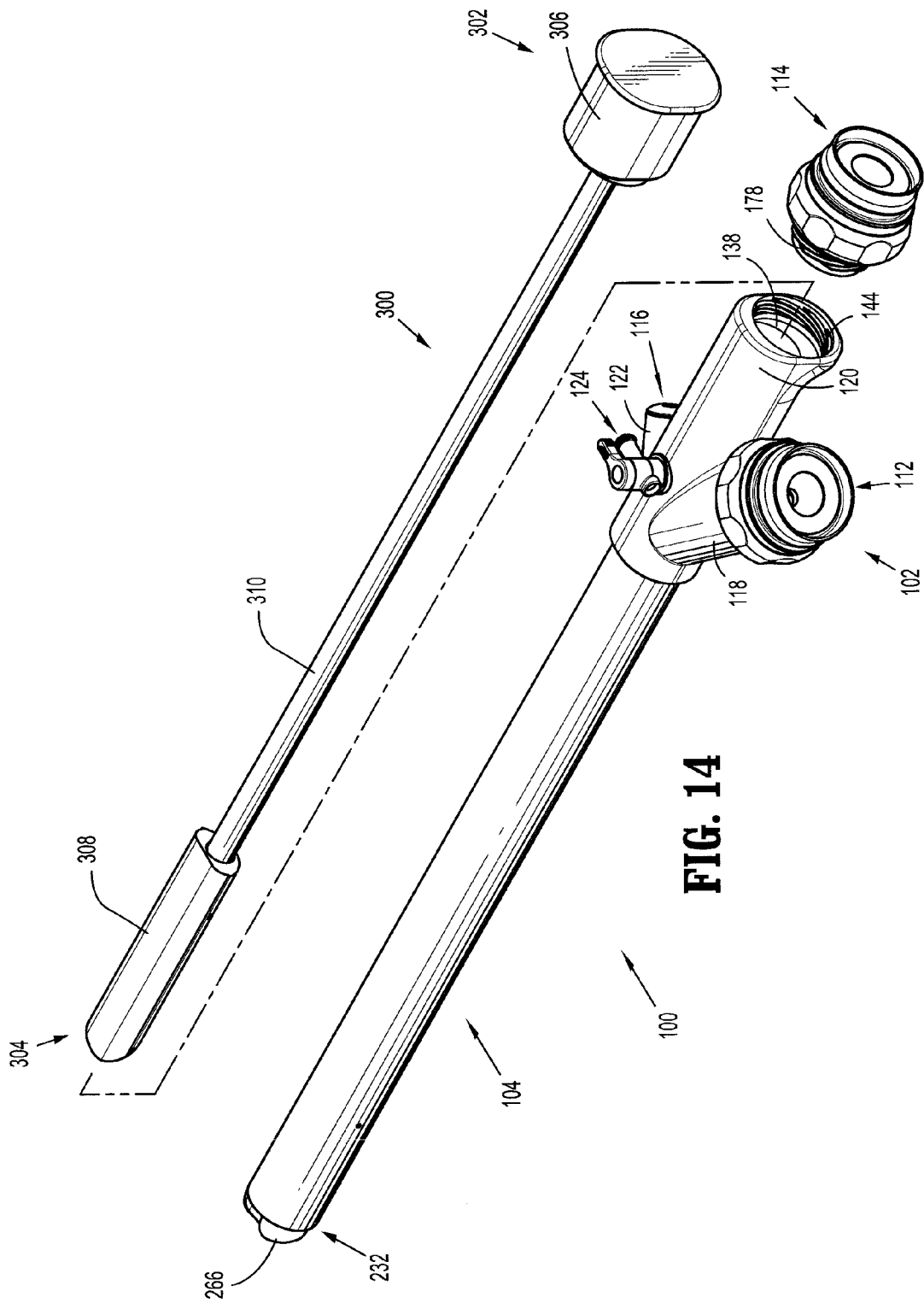
FIG. 14 is a perspective view of an obturator, and the access apparatus shown in FIG. 1 with a seal assembly detached therefrom.

Proximal insertion member 248 includes a hole 254 for facilitating fluid communication between insufflation assembly 124 and lumen 234 of tubular member 104. As seen in FIG. 7, when proximal insertion member 248 is located inside tubular member 104 and housing 102, hole 254 is aligned with opening 242 of tubular member 104 and hole 136 of housing 102. Proximal insertion member 248 defines a channel 256 configured to slidably receive a surgical instrument therethrough. Channel 256 has a longitudinal portion 258 and a curved portion 260. As seen in FIG. 12, curved portion 260 is located at a proximal section of channel 256 and leads to bore 210 of first tubular portion 118 when shaft insert 246 is disposed in lumen 234 of tubular member 104.

Figure 6:
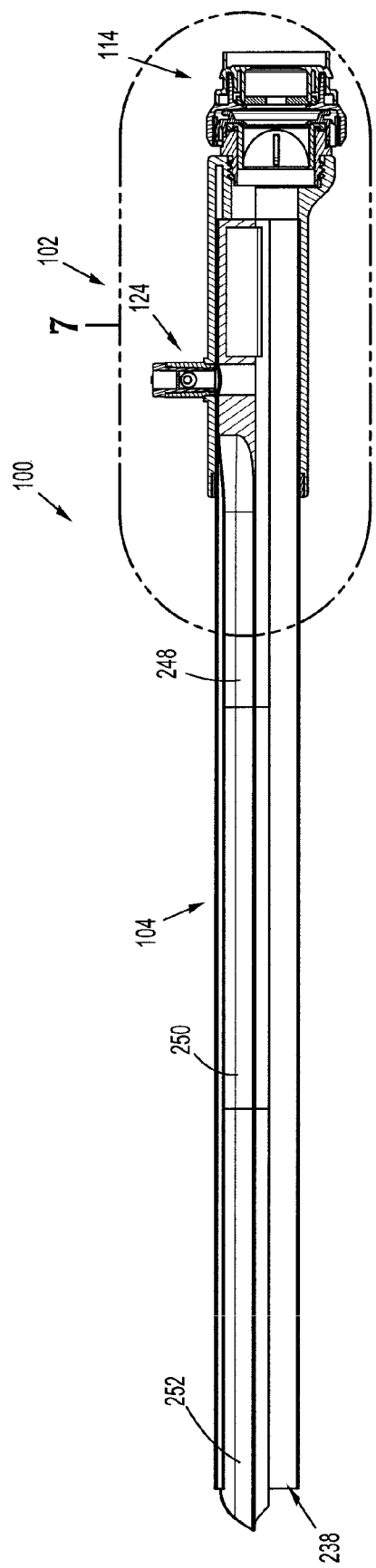
FIG. 6 is a side cross-sectional view of the access apparatus shown in FIG. 1, taken along section line 6-6 of FIG. 3.

As seen in FIGS. 5 and 6, middle insertion member 250 is disposed between proximal insertion member 248 and distal insertion member 252 and defines a longitudinal channel 262. Longitudinal channel 262 extends along the length of middle insertion member 250. When shaft insert 246 and tubular member 104 are positioned in housing 102, longitudinal channel 262 is longitudinally aligned with longitudinal portion 258 of channel 256 of proximal insertion member 248.

Figure 10:
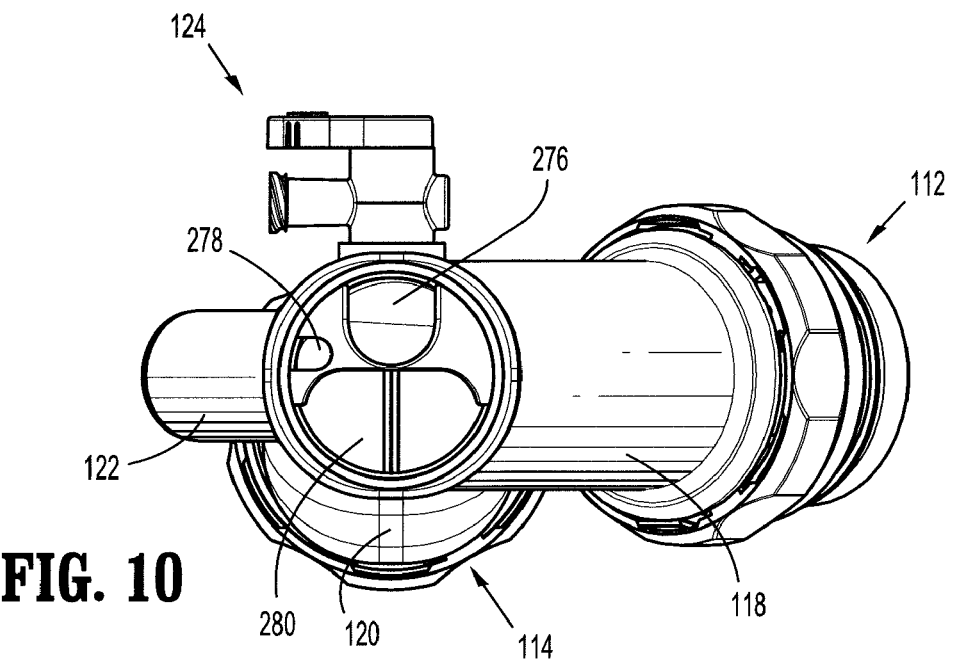
FIG. 10 is a front view of the access apparatus shown in FIG. 1.
Figure 11:
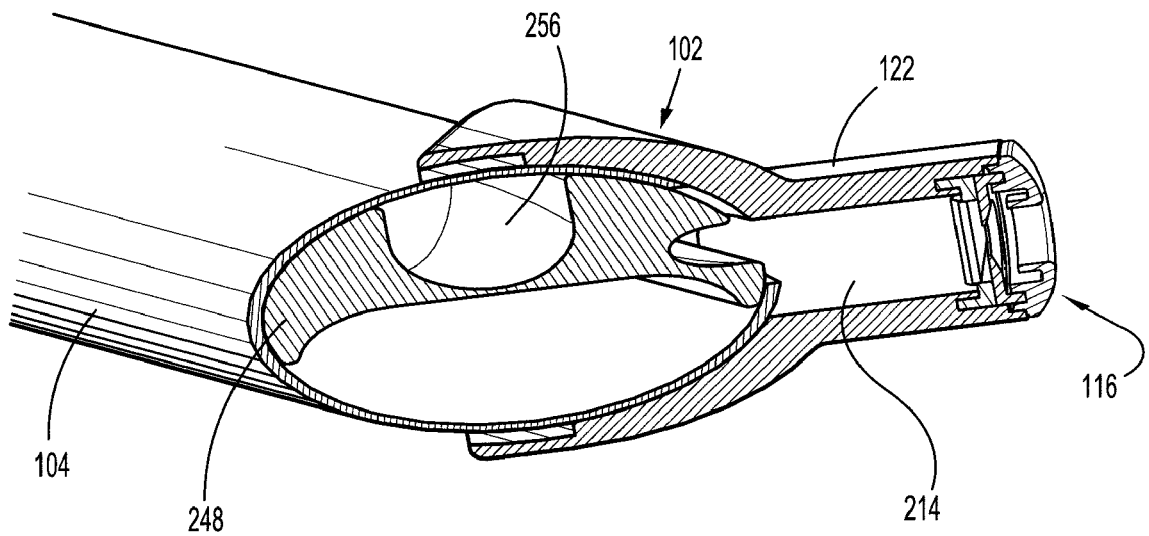
FIG. 11 is a perspective cross-sectional view of the access apparatus shown in FIG. 1, taken along section line 11-11 of FIG. 3.

As seen in FIGS. 5 and 8, distal insertion member 252 also has a longitudinal channel 264 extending therealong. Longitudinal channel 264 aligns with longitudinal channel 262 of middle insertion member 250 when shaft insert 246 and tubular member 104 are connected to housing 102. As seen in FIG. 10, longitudinal channel 264, longitudinal channel 262, and channel 256 together form a passageway 276 disposed in communication with bore 210 of first tubular portion 118 of housing 102. Distal insertion member 252 further includes an atraumatic blunt tip 266 at a distal end 268 thereof. Atraumatic blunt tip 266 prevents or minimizes damage to a patient when access apparatus 100 is inserted into the patient's body.

With reference to FIGS. 8-13, proximal insertion member 248 includes a groove 270 extending along a lateral portion thereof. As seen in FIG. 9, groove 270 is disposed in communication with bore 214 of third tubular portion 122 when tubular member 102 is coupled to housing 102. Middle insertion member 250 also includes a groove 272 positioned laterally therealong. When middle insertion member 250 is connected to proximal insertion member 248, groove 272 of middle insertion member 250 is longitudinally aligned with groove 270 of proximal insertion member 248. Distal insertion member 252 defines a groove 274 extending along a lateral portion thereof. When distal insertion member 252 is coupled to middle insertion member 250, groove 274 of distal insertion member 252 is longitudinally aligned with groove 272 of middle insertion member 250. As seen in FIG. 10, grooves 270, 272, 274 together form a passageway 278 adapted to slidably receive a surgical instrument. In one embodiment, the cross-sectional area of the passageway 278 formed by grooves 270, 272, 274 is smaller than the cross-sectional area of the passageway 276 formed by longitudinal channel 264, longitudinal channel 262, and channel 256, as seen in FIG. 10.

When shaft insert 246 is inserted into lumen 234 of tubular member 104, shaft insert 246 partitions lumen in three passageways 276, 278, 280. (See FIGS. 10 and 13). As discussed above, passageway 276 is connected to bore 270 of first tubular portion 118. Passageway 278 is disposed in communication with bore 214 of third tubular portion 122. Passageway 280 is disposed in communication with bore 138 of second tubular portion 120. In some embodiments, the cross-sectional area of passageway 280 is larger than the cross-sectional areas of passageways 276, 278.

With reference to FIG. 14-20, passageway 280 is configured to accommodate at least a portion of an obturator 300. Obturator 300 has a proximal portion 302 and a distal portion 304 and incorporates a handle 306, an atraumatic blunt tip 308, and a shaft 310. Handle 306 is connected to a proximal end of shaft 310 of obturator 300 and facilitates grasping by a user. Atraumatic blunt tip 308 is connected to a distal end of shaft 310 and aids in the insertion of access apparatus 100 inside a human body while preventing or minimizing damage to the body. In one embodiment, a transverse cross-section of atraumatic blunt tip 308 is substantially similar in profile to a cross-section of passageway 280. In some embodiments, atraumatic blunt tip 308 has a substantially arcuate transverse cross-section.

Figure 15:
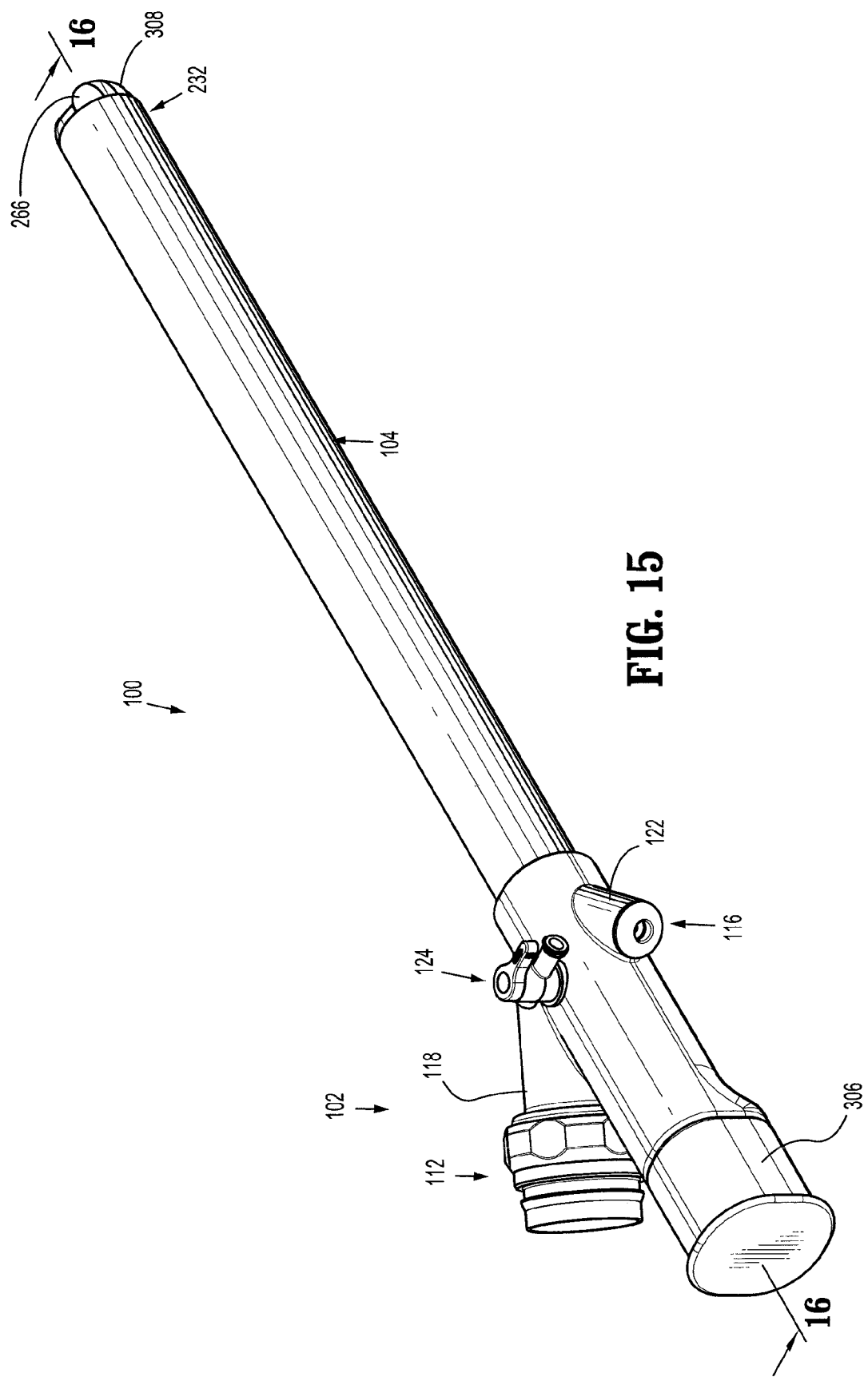
FIG. 15 is a perspective view of the access apparatus shown in FIG. 1 with the obturator depicted in FIG. 14 inserted therein.
Figure 18:
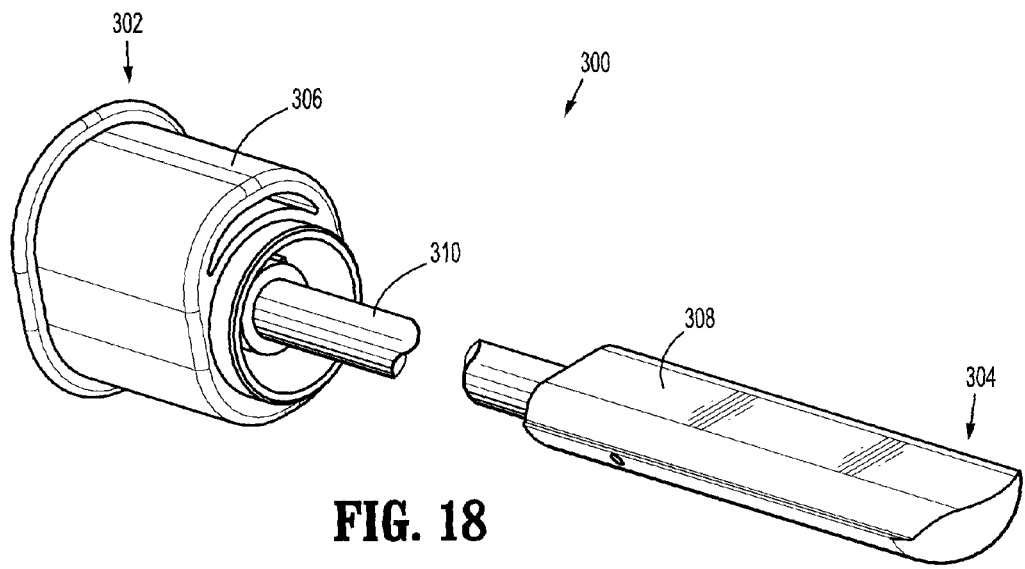
FIG. 18 is a perspective view showing the proximal and distal portions of the obturator depicted in FIG. 14.
Figure 19:
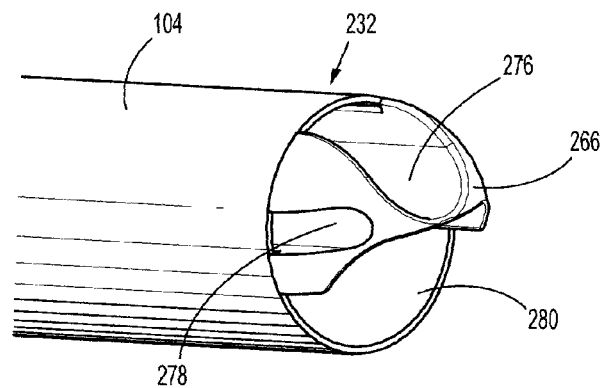
FIG. 19 is a perspective view of a distal portion of the access apparatus shown in FIG. 1 without the obturator being introduced in the access apparatus.
Figure 20:
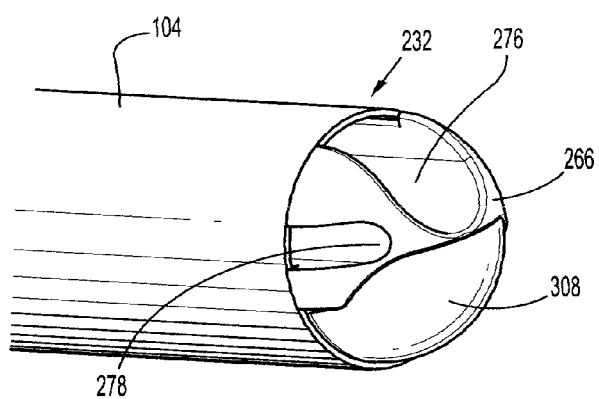
FIG. 20 is a perspective view of the distal portion of the access apparatus shown in FIG. 1 with the obturator inserted into the access apparatus.

Obturator 300 can be inserted inside access apparatus 100 through bore 138 of second tubular portion 120 once the user has removed second seal assembly 114 from housing 102. To detach second seal assembly 114 from housing 102, the user rotates knob 156 of second seal assembly 114 relative to housing 102. As second seal assembly 114 rotates with respect to housing 102, inner thread 175 of second seal assembly disengages inner thread 144 of housing 102, releasing second seal assembly 114 from housing 104. As seen in FIG. 15, after detaching second seal assembly 114 from housing 102, the user introduces obturator 300 into access apparatus 100 through bore 138 until atraumatic blunt tip 308 extends beyond distal portion 232 of tubular member 104. As shown in FIGS. 16 and 17, when obturator 300 is inserted inside access apparatus 100, shaft 310 and a portion of atraumatic blunt tip 308 are disposed in passageway 280. As shown in FIG. 19, before obturator 300 is positioned within access apparatus 100, passageway 280 has a distal open end. However, as depicted in FIG. 20, once obturator 300 is positioned inside access apparatus 100, the distal end of passageway 280 is blocked by atraumatic blunt tip 308.

In operation, a user may use access apparatus 100 in conjunction with obturator 300 for a number of surgical procedures. For example, during one surgical procedure, the user may detach second seal assembly 114 from housing 102, as described above, and the user may then place obturator 300 inside access apparatus 300, as described above. The user may then introduce a tubular member 104 inside a patient's body via a body lumen such as the rectum or the vagina, and the user may then push access apparatus 100 distally until distal portion 232 of tubular member 104 has reached the target surgical site. Once tubular member reaches the target site, the user may then remove obturator 300 from access apparatus and reattach second seal assembly 114 to housing 102. The user reattaches second seal assembly 114 to housing 102 in the manner described above.

Subsequently, the user may connect access apparatus 100 to a source of insufflation gases via insufflation assembly 124. After fluidly coupling access apparatus 100 to a source of insufflation gases, the user may retract body tissue at the target surgical site by insufflating the body cavity with $CO_2$ or any other suitable insufflation gas. Before supplying the target site with insufflation gases, the user moves stop-cock valve 126 to the open position to allow fluid flow through insufflation assembly 124. Following the retraction of body tissue, the user disconnects the source of insufflation gases from insufflation assembly 124.

The user may then insert an endoscope (not shown) through first port 106 and slides the endoscope through passageway 276 until it reaches distal portion 232 of tubular member 104. The endoscope gives the user the capability of observing the target site. While monitoring the target site with the endoscope, the user can also insert one or more surgical instruments through first and/or third ports 106, 110 to simultaneously perform one or more surgical procedures through the same body opening.

Figures 21, 22:
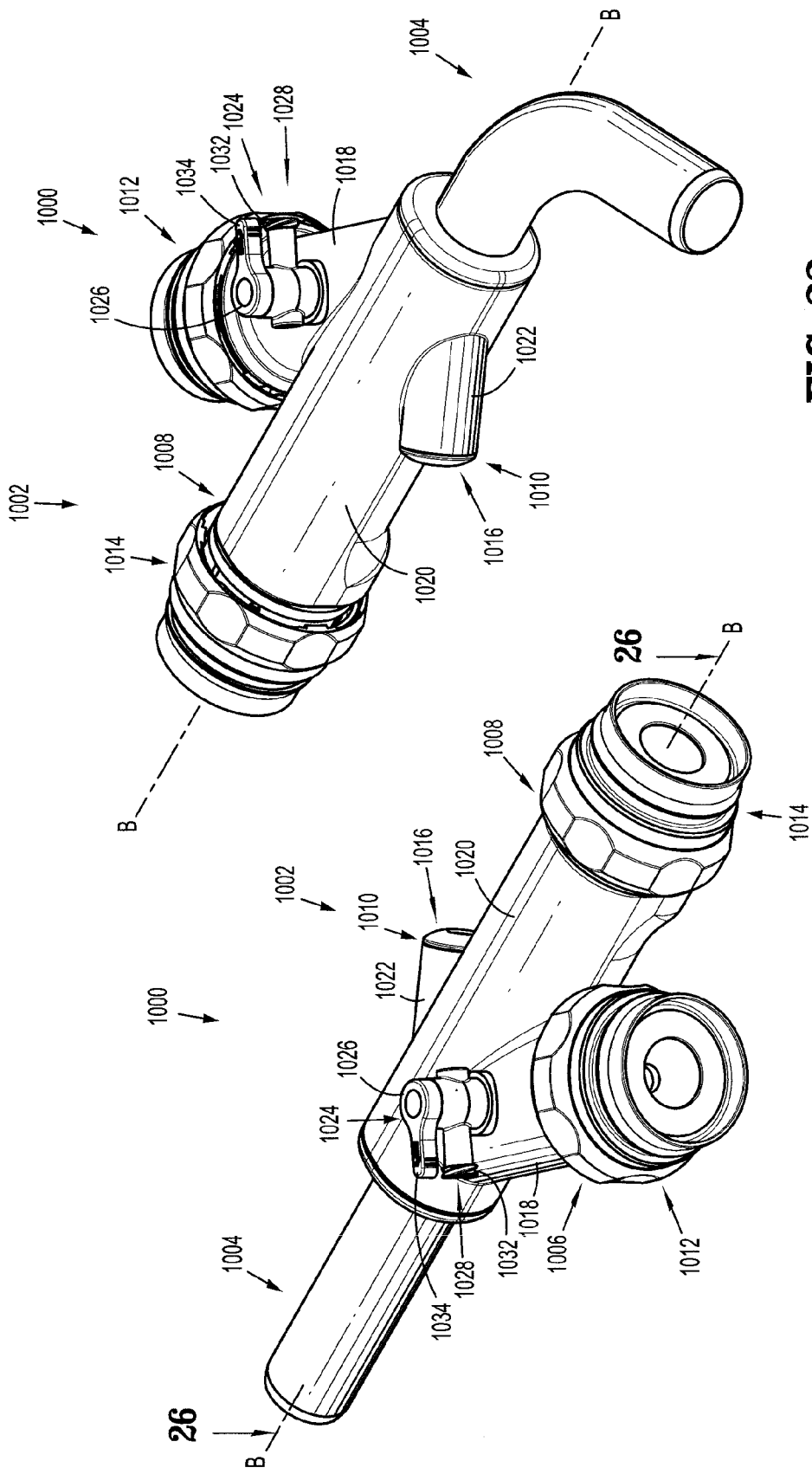
FIG. 21 is a perspective view of an access apparatus with a flexible shaft according to another embodiment of the present disclosure.
FIG. 22 is a perspective view of the access apparatus depicted in FIG. 21 showing the flexible shaft bent relative to the longitudinal axis B-B.
Figure 23:
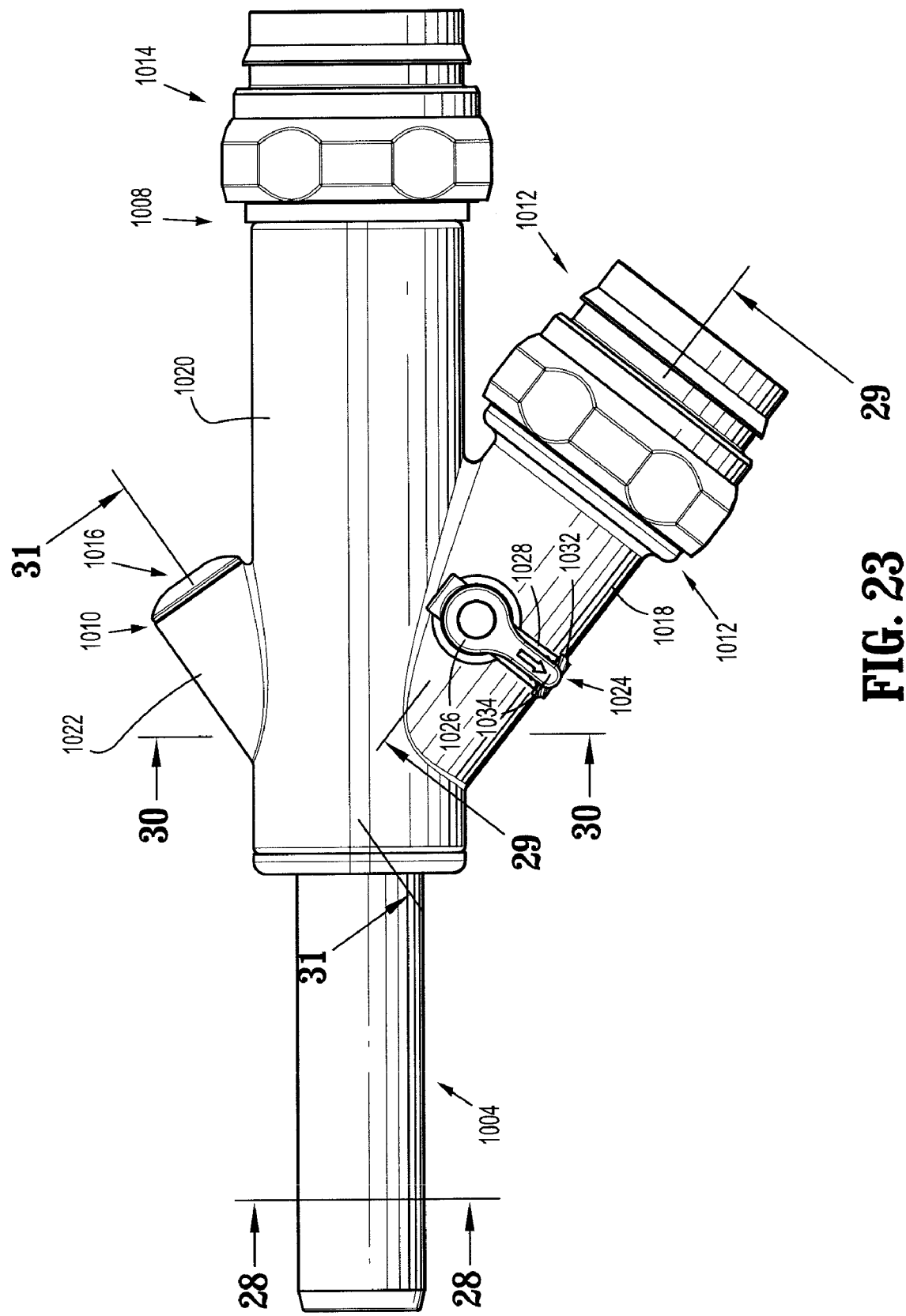
FIG. 23 is a top view of the access apparatus depicted in FIG. 21.

With reference to FIGS. 21-23, an alternate embodiment of access apparatus is designated with reference numeral 1000. Access apparatus 1000 includes a housing 1002 and a tubular member 1004 extending distally from housing 1002. In this embodiment, tubular member 1004 is made of a flexible material. Tubular member 1004 defines a longitudinal axis B-B when oriented in a straight position, as seen in FIG. 21. Tubular member 1004 is capable of bending with respect to longitudinal axis B-B. (See FIG. 22). The structure and operation of housing 1002 is substantially similar to housing 102 of access apparatus 100.

Housing 1002 includes a first tubular portion 1018, a second tubular portion 1020, and a third tubular portion 1022. First tubular portion 1018 is oriented substantially parallel to longitudinal axis B-B. Second and third tubular portions 1020, 1022 converge into first tubular portion 1018 and each is define an axis that is at an oblique angle relative to longitudinal axis B-B.

First tubular portion 1018 includes a first port 1006 adapted to receive a surgical instrument and at least a portion of a first seal assembly 1012. Second tubular portion 1020 includes a second port 1008 adapted to receive a surgical instrument and at least a portion of a second seal assembly 1014. Third tubular portion 1022 includes a third port 1010 adapted to receive a surgical instrument and at least a portion of a third seal assembly 1016. First, second, and third seal assemblies 1012, 1014, 1016 form a fluid-tight seal around a surgical instrument when said surgical instrument is inserted through first, second, and third ports 1006, 1008, 1010, respectively.

Figure 30:
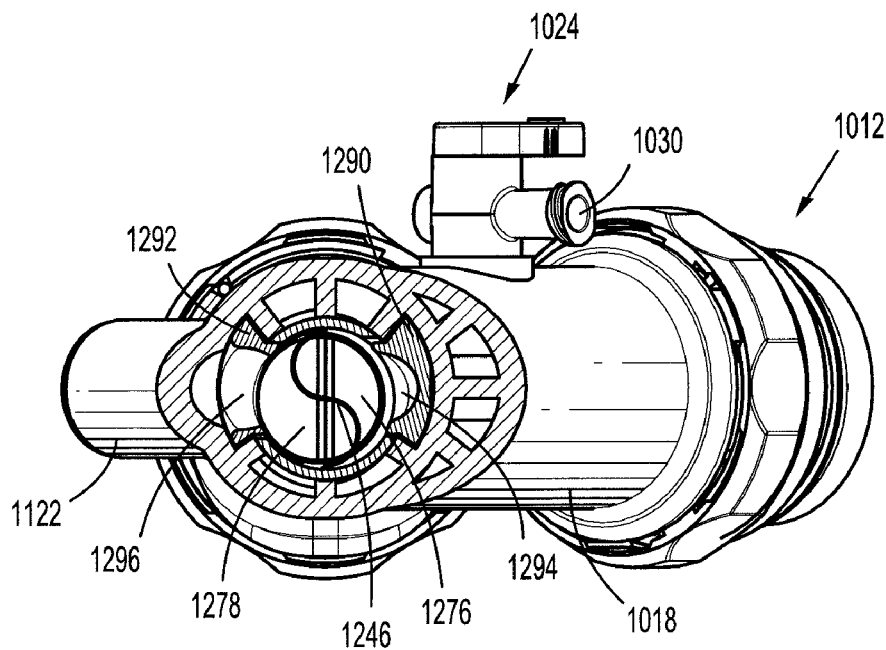
FIG. 30 is a front cross-sectional view of the access apparatus depicted in FIG. 21, taken along section line 30-30 of FIG. 23.
Figure 31:
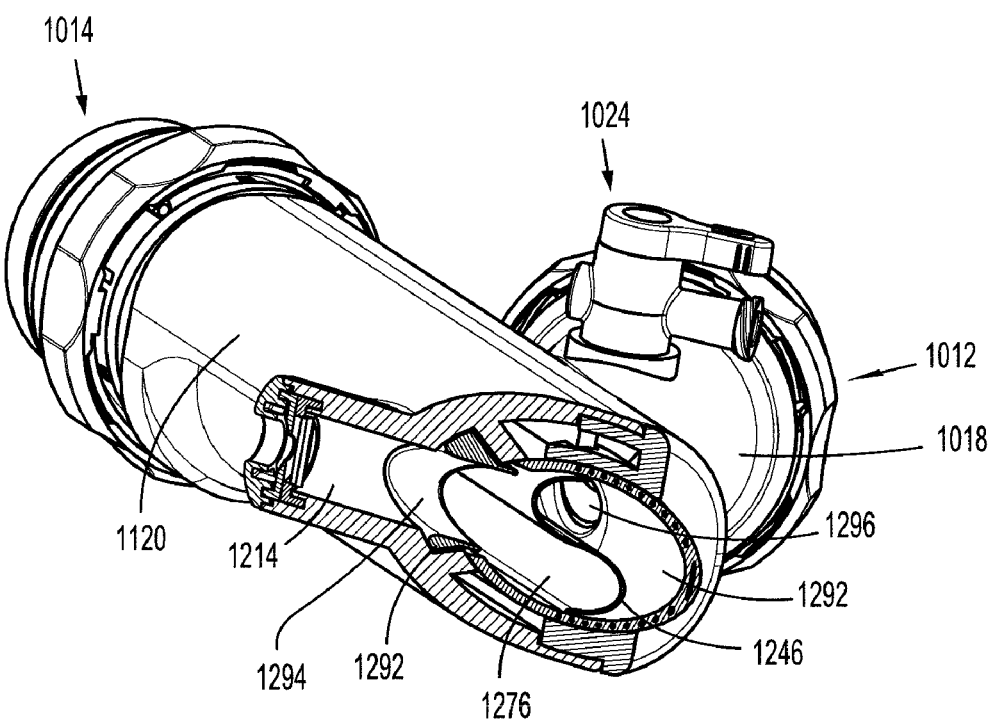
FIG. 31 is a perspective cross-sectional view of the access apparatus depicted in FIG. 21, taken along section line 31-31 of FIG. 23.

Housing 1002 further includes an insufflation assembly 1024 configured to be connected to a source of insufflation gases or a vacuum system (not shown). Insufflation assembly 1024 includes an insufflation port 1028 and a stop-cock valve 1026. Insufflation port 1028 defines a lumen 1030 (see FIG. 30) disposed in fluid communication with an inner portion of housing 1002 and includes an external thread 1032 for facilitating connection to a source of insufflation gases or a vacuum system.

Stopcock valve 1026 has an open position and closed position and is therefore capable of controlling fluid flow through insufflation assembly 1024. In the open position, stopcock valve 1026 allows fluid flow through insufflation assembly 1024. In the closed position, stopcock valve 1026 prevents or hinders fluid flow through insufflation assembly 1024. In one embodiment, stopcock valve 1026 includes a lever 1034 extending therefrom. Lever 1034 facilitates rotation of stopcock valve 1026 with respect to housing 202 between the open and closed positions. In the depicted embodiment, insufflation assembly 1024 is positioned on first tubular member 1018. In use, a user actuates stopcock valve 1026 between the open and closed positions by rotating stopcock valve 1026 relative housing 1002 through lever 1034.

With reference to FIGS. 24-31, first tubular member 1018 has an opening 1036 configured to receive a portion of insufflation assembly 1024. Opening 1036 is disposed in fluid communication with insufflation port 1028 and a bore 1210 defined through first tubular member 1018. In operation, Opening 1036 permits fluid exchange between bore 1028 and a source of insufflation gases or vacuum system fluidly coupled to insufflation assembly 1024.

Figures 24, 25:
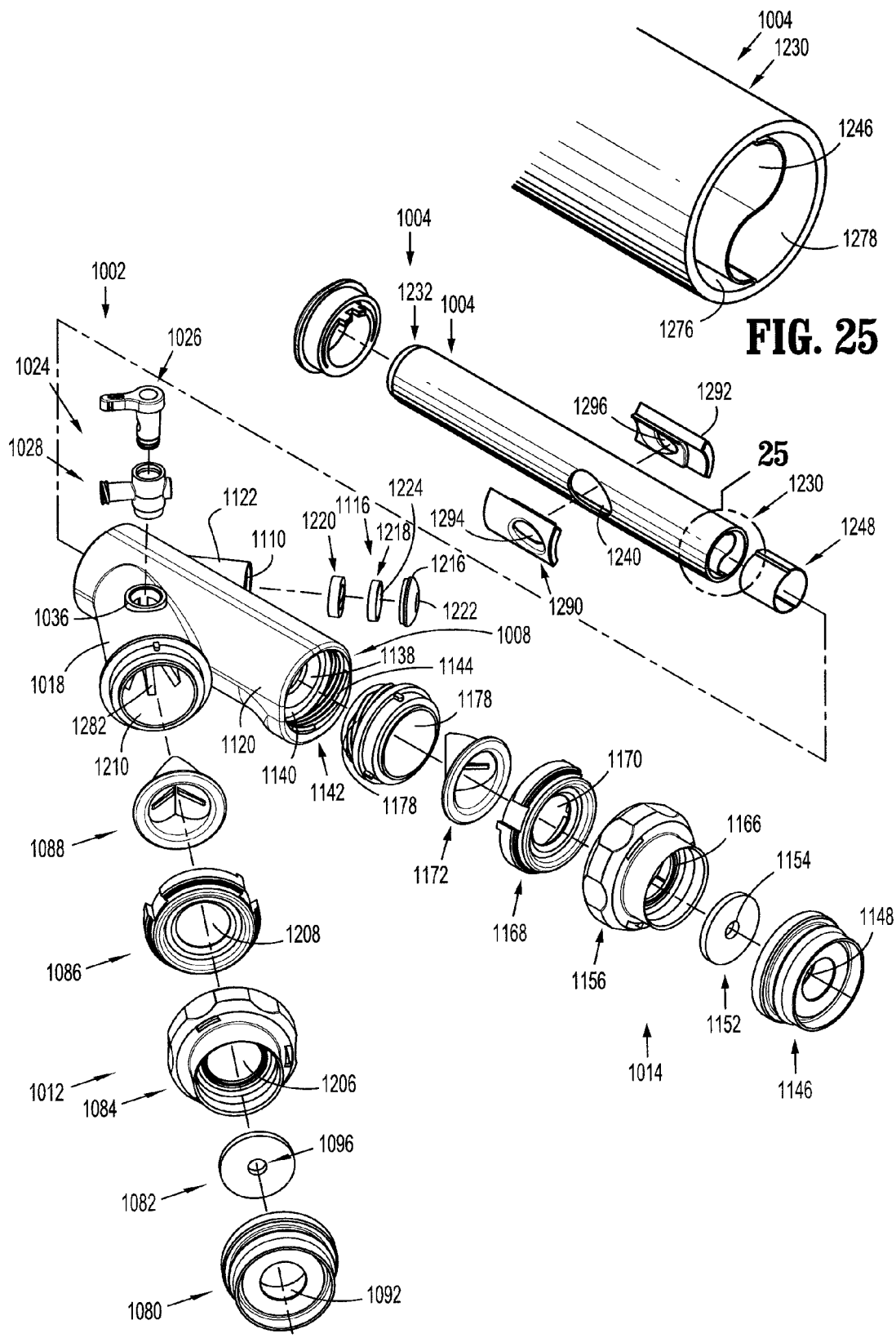
FIG. 24 is a perspective view, with parts separated, of the access apparatus depicted in FIG. 21.
FIG. 25 is an enlarged view of the indicated area of detail of FIG. 24.
Figures 26, 27:
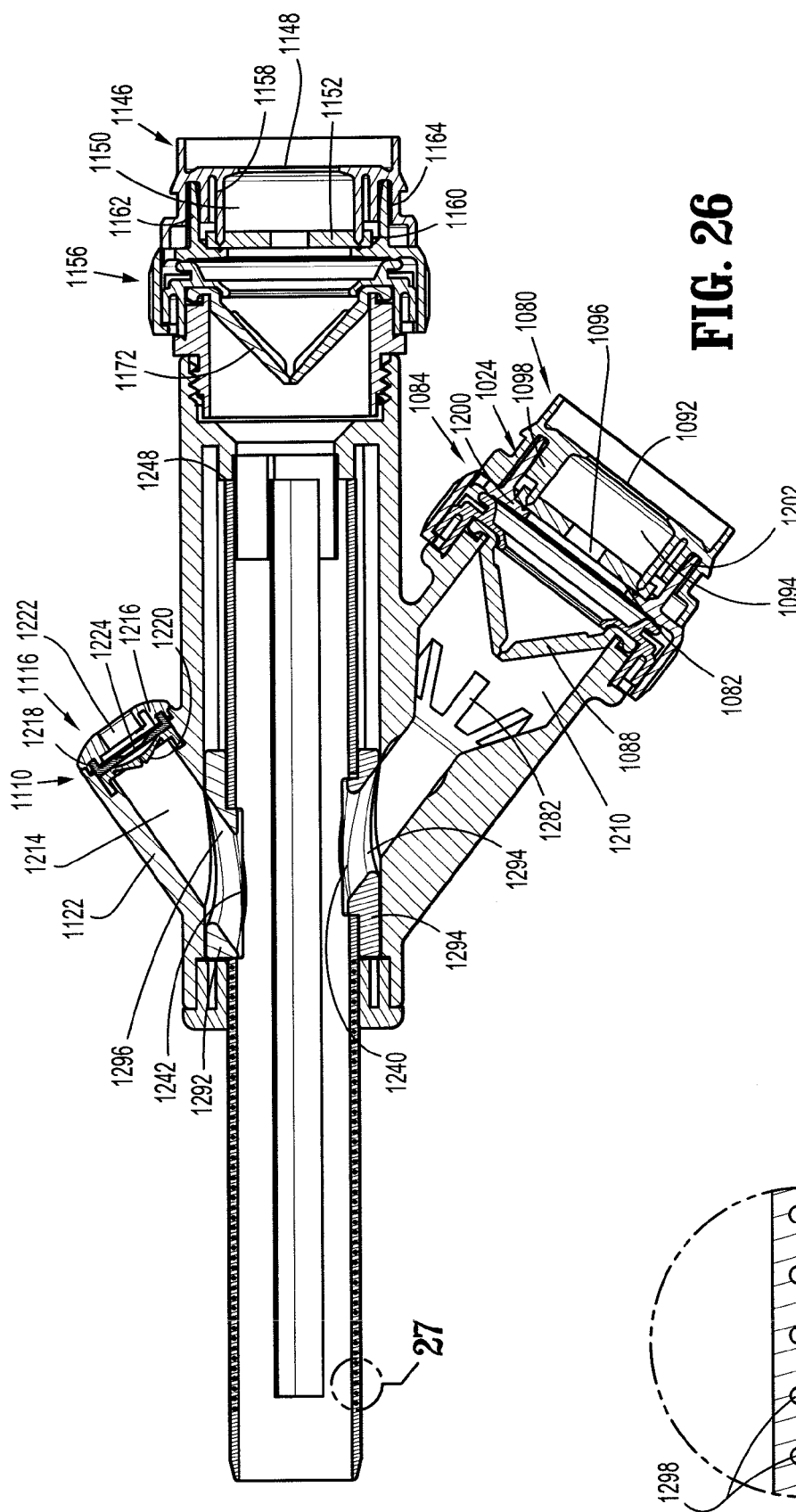
FIG. 26 is a side cross-sectional view of the access apparatus depicted in FIG. 21, taken along section line 26-26 of FIG. 21.
FIG. 27 is an enlarged view of the indicated area of detail of FIG. 26.
Figure 29:
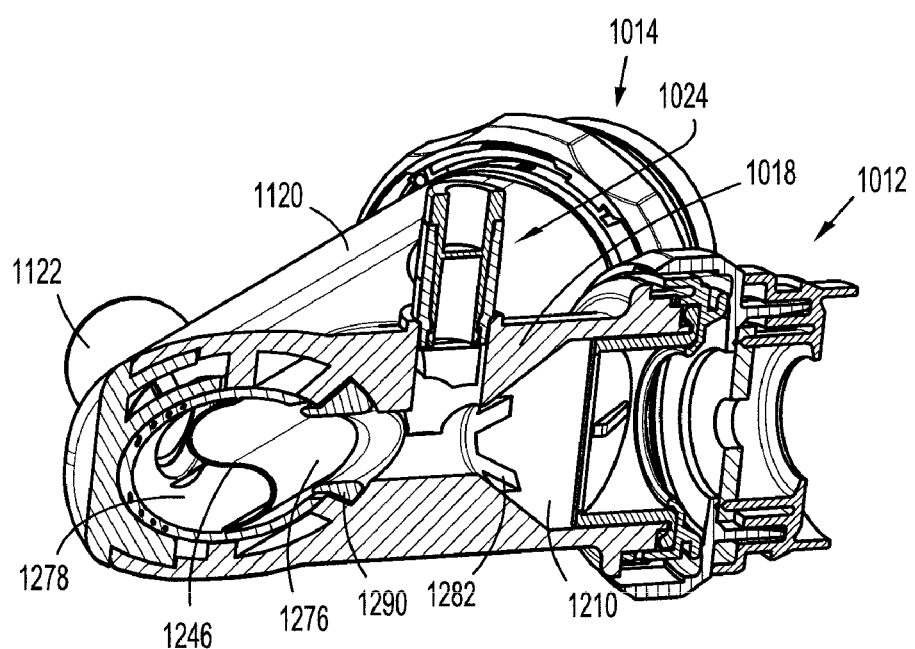
FIG. 29 is a perspective cross-sectional view of the access apparatus depicted in FIG. 21, taken along section line 29-29 of FIG. 23.

As seen in FIGS. 24, 26, and 29, first tubular portion 1018 further includes a plurality of ribs 1282 disposed around bore 1210. Ribs 1282 facilitate the insertion of a surgical instrument through bore 1210. Bore 1210 is configured to accommodate at least a portion of first seal assembly 1012.

As seen in FIGS. 24 and 26, first seal assembly 1012 is fixed to first tubular member 1018. First seal assembly 1012 includes a cover 1080, an instrument seal 1082, a knob 1084, a seal cover 1086, and a duckbill valve 1088. Cover 1080 defines an opening 1092 extending therethrough. Opening 1092 is dimensioned to receive a surgical instrument and leads to an inner cavity 1094 (see FIG. 26) of cover 1080. Inner cavity 1094 is configured to receive instrument seal 1082. Instrument seal 1082 defines an aperture 1096 extending therethrough. Aperture 1096 is dimensioned to receive a surgical instrument. In use, instrument seal 1082 forms a fluid-tight seal around a surgical instrument inserted through aperture 1096.

First seal assembly 1012 can be connected to port 1006 by snapping knob 184s onto port 1006. It is envisioned, however, that first seal assembly 1012 may be connected to port 1006 by any suitable means. When first seal assembly 1012 is assembled, instrument seal 1082 is located between cover 1080 and knob 1084. As seen in FIG. 26, instrument seal 1082 includes a ring 1098 protruding distally therefrom. Ring 1098 presses instrument seal against a proximal wall 1200 of knob 1084. Knob 1084 includes a ring 1202 protruding proximally therefrom. Ring 1202 is adapted to be received inside an annular space 1204 formed in cover 1080. During assembly, ring 1202 is positioned inside annular space 1204 to facilitate interconnection between cover 1080 and knob 1084.

Knob 1084 includes a longitudinal opening 1206 configured to receive a surgical instrument and at least a portion of seal cover 1086. Seal cover 1086 includes a hole 1208 adapted to receive a surgical instrument. During operation, seal cover 1086 helps secure duckbill valve 1088 to first seal assembly 1012 and first tubular member 1018. Duckbill valve 1088 is partially disposed in bore 1210 of first tubular portion 1018. In operation, duckbill valve 1088 forms a fluid-tight seal around a surgical instrument inserted therethrough and closes in the absence of a surgical instrument extending therethrough.

As seen in FIG. 24, second tubular portion 1120 of housing 1002 has inner surfaces 1140 forming a bore 1138. Bore 1138 extends through second tubular portion 1120 and is configured to receive a portion of tubular member 1004 and a portion of second seal assembly 1014. Second tubular portion 1120 further includes an inner thread 1144 formed about a proximal end 1142 of inner surface 1140. Inner thread 1144 is configured to threadedly engage a portion of second seal assembly 1014.

Second seal assembly 1014 is substantially identical in construction and operation as second seal assembly 1014 of access apparatus 100 and thus will not be described in further detail herein. Like ports of second seal assembly 1014 will be identified with like reference characters as second seal assembly 114.

As seen in FIGS. 24 and 26, third tubular portion 1122 of housing 1002 defines a bore 1214 dimensioned to receive a surgical instrument. Bore 1214 is disposed in fluid communication with third port 1110. Third seal assembly 1016 covers third port 1110 and includes cap 1216, an instrument seal 218, and a duckbill valve 1220. Cap 1216 has a hole 1222 extending therethrough. Hole 1222 is dimensioned to receive a surgical instrument and leads to bore 1214 of third tubular portion 1122. Instrument seal 1218 is secured between cap 1216 and duckbill valve 1222 and defines an opening 1224. Opening 1224 is configured to receive a surgical instrument. In use, instrument seal 1218 forms a fluid-tight seal around a surgical instrument inserted through opening 1224. Duckbill valve 1220 is adapted to form a fluid-tight seal around a surgical instrument inserted therethrough and close in the absence of a surgical instrument.

Figure 28:
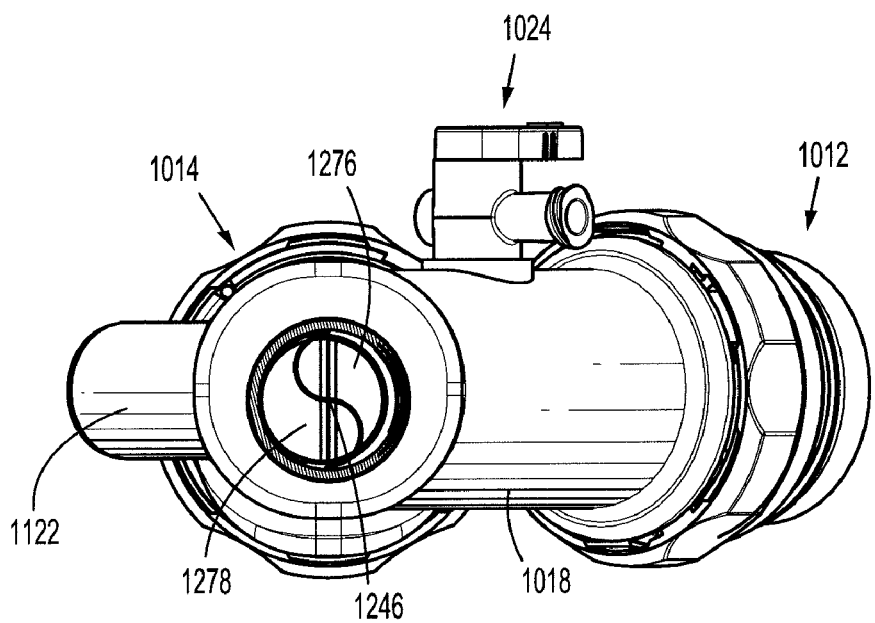
FIG. 28 is a front cross-sectional view of the access apparatus depicted in FIG. 21, taken along section line 28-28 of FIG. 23.

As seen in FIGS. 24-26, tubular member 1004 has a proximal portion 1230 and a distal portion 1232. Proximal portion 1230 is positioned inside second tubular portion 1120 of housing 1002. In addition, tubular member 1004 includes a dividing wall 1246 extending therethrough. In one embodiment, dividing wall 1246 has a substantially S-shaped transverse cross-sectional profile. It is contemplated that dividing wall 1246 may have a sinusoidal, zig-zag, C-shaped, triangular, straight, diagonal or any other suitable transverse cross-sectional profile. In an embodiment, dividing wall 1246 is made of a flexible and/or resilient material. Dividing wall 1246 divides the inner cavity of tubular member 1004 into first and second passageways 1276, 1278, as depicted in FIG. 28.

As seen in FIGS. 24 and 26, a sleeve 1248 is partially poisoned within proximal portion 1230 of tubular member 1004. As seen in FIG. 26, another portion of sleeve 1248 is disposed inside bore 1138 of first tubular portion 1120. Sleeve 1248 facilitates interconnection between tubular member 1004 and housing 1002.

As shown in FIGS. 24 and 26, tubular member 1004 further includes a lateral aperture 1240 for establishing fluid communication between bore 1210 of first tubular portion 1210 and passageway 1276 of tubular member 1004. In addition, tubular member 1004 includes another lateral aperture 1242 for establishing fluid communication between bore 1214 of third tubular portion 1122 and passageway 1275 of tubular member 1004. Lateral aperture 1242 is disposed in diametrically opposed relation to lateral aperture 1240.

As shown in FIGS. 24 and 26, access apparatus 1000 also includes a pair of fittings 1290, 1292 each adapted to partially cover a lateral aperture 1240, 1242. Fitting 1290 is positioned between housing 1002 and tubular member 1004 and helps secure tubular member 1004 to housing 1002. Moreover, fitting 1290 defines a hole 1294 aligned with lateral aperture 1240. Fitting 1292 is also disposed between housing 1002 and tubular member 1004 and aids in securing tubular member 1004 to housing 1002. Further, fitting 1292 includes a hole 1296 aligned with lateral aperture 1242 of tubular member 1004.

As discussed above, at least a portion of tubular member 1004 is made of a flexible and/or resilient material such as, for example an elastomer, stainless steel wire, shape-memory alloys, polycarbonate, etc. In the embodiment depicted in FIGS. 26 and 27, tubular member 1004 includes one or more strands 1298 embedded in or connected to a portion thereof. Strands 1298 are made of a flexible and/or resilient material. As seen in FIG. 26, strands 1298 surround a portion of tubular member 1004. In one embodiment, strands 1295 are made of a resilient material that helps maintain tubular 1004 in a straight position or in a bent position after being manually bent by the user.

In operation, a user inserts access apparatus 1000 into a patient through a body lumen or via an incision. Then, the user advances access apparatus 1000 toward the target body cavity. Optionally, the user insufflates the target body cavity with insufflation gases. To insufflate the target body cavity, the user fluidly connects access apparatus 1000 to a source of insufflation gases via insufflation assembly 1024. Before, after, or during insertion of access apparatus 1000, the user may bend tubular member 1004 manually to reach the target body cavity. Next, the user activates the source of insufflation gases to expand the body cavity. The user may then introduce one or more surgical instruments through first, second, and/or third seal assemblies 1012, 1014, 1016.

It will be understood that various modifications can be made to the embodiments disclosed herein. For example, tubular members 1004 of various sizes may be connected to housing 1004. Therefore, the above description should not be construed as limiting, but merely as exemplifications of embodiments. Those skilled in the art will envision other modifications within the scope and spirit of the present disclosure.

What is claimed is:

1. A surgical access apparatus for providing access inside a body, comprising:
    a housing having a first port;
    a tubular member extending distally from the housing and defining a longitudinal axis therealong, wherein the tubular member includes a lumen extending therethrough;
    a shaft insert disposed in the lumen of the tubular member, the shaft insert including a series of grooves formed in an outer surface thereof, wherein the shaft insert forms first, second, and third passageways between the grooves and an inner surface of the lumen of the tubular member, the first, second and third passageways extending along the lumen of the tubular member, wherein each of the first, second, and third passageways is adapted to receive a surgical instrument, the shaft insert including an atraumatic blunt tip at a distal end thereof and extending distally of the tubular member; and
    a first seal assembly covering the first port of the housing and defining a first passage disposed in communication with the first passageway defined by the shaft insert in the tubular member, wherein the first seal assembly is adapted to form a seal around the surgical instrument inserted through the first passage of the first seal assembly.

2. The access apparatus according to claim 1, wherein the tubular member is made of a one of rigid material and a flexible material.

3. The access apparatus according to claim 1, wherein the housing includes a first tubular portion defining an axis that is at an oblique angle relative to the longitudinal axis of the tubular member.

4. The access apparatus according to claim 3, wherein the first tubular portion of the housing includes a bore disposed in fluid communication with the first port.

5. The access apparatus according to claim 1, wherein the housing includes a second port and a third port, each of the second and third ports being adapted to receive a surgical instrument.

6. The access apparatus according to claim 5, wherein the housing includes a second tubular portion having a bore, the bore being disposed in communication with the second port and the second passageway.

7. The access apparatus according to claim 6, wherein the second tubular portion of the housing defines an axis that is oriented substantially parallel to the longitudinal axis of the tubular member.

8. The access apparatus according to claim 6, further comprising a second seal assembly releasably connected to the second tubular portion of the housing, the second seal assembly having passage disposed in communication with the second passageway, wherein the seal assembly is adapted to form a seal around a surgical instrument inserted through the second passage.

9. The access apparatus according to claim 6, wherein the second passageway is configured to receive an obturator in the absence of the second seal assembly.

10. The access apparatus according to claim 7, wherein the housing includes a third tubular portion having a bore, the bore being disposed in communication with the third port and the third passageway.

11. The access apparatus according to claim 10, wherein the third tubular portion of the housing defines an axis that is at an oblique angle relative to the longitudinal axis of the tubular member.

12. The access apparatus according to claim 10, wherein the third passageway is configured to receive an endoscope.

13. A surgical access apparatus for providing access inside a body, comprising:
    a housing having a first port;
    a tubular member extending distally from the housing and defining a longitudinal axis therealong, wherein the tubular member includes a lumen extending therethrough;
    a dividing wall positioned along the lumen of the tubular member, the dividing wall having a substantially S-shaped transverse cross-sectional profile, wherein the dividing wall divides the lumen into first and second passageways, wherein each of the first and second passageways is adapted to receive a surgical instrument; and
    a first seal assembly covering the first port of the housing and defining a first passage disposed in communication with the first passageway defined by the dividing wall, wherein the first seal assembly is adapted to form a seal around the surgical instrument inserted through the first passage of the first seal assembly.

14. The access apparatus according to claim 13, wherein the tubular member is made of a one of rigid material and a flexible material.

15. The access apparatus according to claim 13, wherein the housing includes a first tubular portion defining an axis that is at an oblique angle relative to the longitudinal axis of the tubular member.

16. The access apparatus according to claim 15, wherein the first tubular portion of the housing includes a bore disposed in fluid communication with the first port.

17. The access apparatus according to claim 13, wherein the housing includes a second port and a third port, each of the second and third ports being adapted to receive a surgical instrument.

18. The access apparatus according to claim 17, wherein the housing includes a second tubular portion having a bore, the bore being disposed in communication with the second port and the second passageway.

19. The access apparatus according to claim 18, wherein the second tubular portion of the housing defines an axis that is oriented substantially parallel to the longitudinal axis of the tubular member.

20. The access apparatus according to claim 13, wherein the dividing wall is made of at least one of a flexible and resilient material.

* * * * *